(12) United States Patent
Kitao et al.

(10) Patent No.: US 7,081,522 B2
(45) Date of Patent: Jul. 25, 2006

(54) GENE CAUSATIVE OF ROTHMUND-THOMSON SYNDROME AND GENE PRODUCT

(75) Inventors: Saori Kitao, Kanagawa (JP); Akira Shimamoto, Kanagawa (JP); Yasuhiro Furuichi, Kanagawa (JP)

(73) Assignee: Agene Research Institute Co., Ltd., Kamakura-shi (JP)

( * ) Notice: Subject to any disclaimer, the term of this patent is extended or adjusted under 35 U.S.C. 154(b) by 0 days.

(21) Appl. No.: 09/889,325

(22) PCT Filed: Jan. 19, 2000

(86) PCT No.: PCT/JP00/00233

§ 371 (c)(1),
(2), (4) Date: May 8, 2003

(87) PCT Pub. No.: WO00/43522

PCT Pub. Date: Jul. 27, 2000

(65) Prior Publication Data

US 2004/0224312 A1    Nov. 11, 2004

(30) Foreign Application Priority Data

Jan. 19, 1999    (JP) .................................. 11-011218

(51) Int. Cl.
*C07K 16/00*    (2006.01)
*C12P 21/08*    (2006.01)
(52) U.S. Cl. .................................. 530/388.1; 530/387.1
(58) Field of Classification Search .............. 530/387.1
See application file for complete search history.

(56) References Cited

U.S. PATENT DOCUMENTS 6,090,620 A * 7/2000 Fu et al. ...................... 435/325
6,335,435 B1   1/2002 Shimamoto et al.
6,472,513 B1 * 10/2002 Shimamoto et al. ... 530/388.26

OTHER PUBLICATIONS

Puranam et al (J. Biol Chem. Nov. 1994; 269(47):29838-29845).*
Harlow Antibodies: A laboratory Manual, 1998; Chapter 5 p. 76.*
Kitao et al (Genomics 1998; 54(3):443-452).*
Campbell (Monoclonal Antibody Technology; 1984; Elsevier Science Publishing Company Inc: pp. 1-33).*
Saori K et al. "Rothmund-Thomson syndrome responsible gene, RECQL4: Genomic structure and products" Genomics, vol. 61, No. 3 (Nov. 1999) p. 268-276 (to be provided).
Kazutsune Y. et al. "Bloom's and Werner's syndrome suppress hyperrecombination in yeast sgs1 mutant: Implication for genomic instability in human diseases", Proc.Natl.Acad. Sci.U.S.A. vol. 95, No. 15, (1998) p. 8733-8738 (to be provided).
Overbeek, PA et al., "Transgenic Animal Technology: A Laboratory Handbook," Factors affecting transgenic animal production, pp. 96-98 (1994).
Wall, RJ. "Transgenic Livestock: Progress and Prospects for the Future," *Thenogenology*, vol. 45, No. 1, pp. 57-68 (1996).
Houdebine, L., "Production of pharmaceutical proteins from transgenic animals," *J. Biotech*. vol. 34, No. 3, pp. 269-287 (1994).
Kappel CA et al., "Regulating gene expression in transgenic animals," *Curr Opin Biotech*, vol. 3, No. 5, pp. 548-553 (1992).
Cameron ER, "Recent Advances in Transgenic Technology," *Mol. Biotech*, vol. 7, No. 3, pp. 253-265 (1997).
Nieman II., "Transgenic farm animals get off the ground," *Transgenic Res.*; vol. 7, No. 1, pp. 73-75 (1998).
Mullins JJ. and Mullins, L. "Transgenesis in Nonmurine Species," *Hypertension*, vol. 22, No. 4, pp. 630-633 (1993).
Mullins, JJ. et al., "Fulminant hypertension in transgenic rats harbouring the mouse Ren-2 gene," *Nature*, vol. 344, No. 6266, pp. 541-544 (1990).
Hammer, R. et al., "Spontaneous Inflammatory Disese in Transgenic Rats Expressing HLA-B27 and Human B2m: An Animal Model of HLA-BS&-Associated Human Disorders," *Cell* vol. 63, pp. 1099-1112 (1990).
Mullins, JJ, et al., "Expression of the DBA/2J Ren-2 gene in the adrenal gland of transgenic mice," *EMBO J* vol. 8, No. 13, pp. 4065-4072 (1989).
Taurog, JD. et al., "HLA-B27 in Inbred and Non-inbred Transgenic Mice," *J. Immunol.*, vol. 141, No. 11, pp. 4020-4023 (1988).
Mullins, L and Mullins, JJ. "Perspective Series: Molecular Medicine In Genetically Engineered Animals," *J. Clin. Invest.*, vol. 98, No. 11, pp. S37-S40 (1996).
Lindor, NM et al., "Rothmund-Thomson Syndrom in Siblings: Evidence for Acquired *In Vivo* Mosaicism", *Clinical Genetics*, 1996, 49:124-129.

(Continued)

*Primary Examiner*—Christopher Yaen
(74) *Attorney, Agent, or Firm*—Banner & Witcoff, Ltd.

(57) ABSTRACT

The RecQ4 helicase gene, belonging to the RecQ helicase gene family, is revealed herein to be the causative gene of Rothmund-Thomson syndrome. The present inventors found out that it is possible to diagnose Rothmund-Thomson syndrome by detecting mutation of this gene. Further, they uncovered that it is possible to treat patients of Rothmund-Thomson syndrome by utilizing normal RecQ4 helicase gene or proteins thereof.

1 Claim, 7 Drawing Sheets

OTHER PUBLICATIONS

Miozzo, M. et al., "Chromosomal Instability in Fibroblasts and Mesenchymal Tumors from 2 SIBS with Rothmund-Thomson Syndrome", *Int. J. Cancer*, 77, pp. 504-510 (1998).

Kitao, Saori, et al., Cloning of Two New Human Helicase Genes of the RecQ Family: Biological Significance of Multiple Species in Higher Eukaryotes, Genomics, 1998, pp. 443-452, vol. 54, No. 3, Academic Press, USA.

Kitao, Saori, et al., Discovery of Gene Responsible for Rothmund-Thomson Syndrome, Jikken Igaku (Experimental Medicine), 1999, pp. 1237-1240, vol. 17, No. 10, AGENE Research Institute, Japan.

Kitao, Saori, et al., Mutations in RECQL4 Cause a Subset of Cases of Rothmund-Thomson Syndrome, Nature Genetics, 1999, pp. 82-84, vol. 22, No. 1, Nature America Inc., USA.

* cited by examiner

SEQUENCE LISTING

<160> NUMBER OF SEQ ID NOS: 46

<210> SEQ ID NO 1
<211> LENGTH: 679
<212> TYPE: DNA
<213> ORGANISM: Homo sapiens

<400> SEQUENCE: 1
agatctcaac gatcatactc gctctgacag gacagaccaa ccgagcactt gtcacgggag      60
aacaccaaag cagacggcct gcccaccaag ggaggcaggc acctccgtgc gacgccccct     120
cccctcccgc cggccgcagg gaacgcgacg gtcctcggtc gcctgcgttt cgcgaagacg     180
cccccgcccg gctcctccgg gcctcgagcc gcgggaggcg ctggaccctc cgctctttcg     240
cctcccgagc ggggcctgct cctccaggtc ggatgcgtct cccaccaggg cctgacgccg     300
ctccgaccgg cccggggact cccagtcctt cccggcccgc ggtggcacct cccaggctcc     360
cggcctcggc cccgggctcc caaatgcagc cactgcctcc ctcggccagg ccgccccgag     420
cgaccggtgc cccgccccct tgaggccagg cagggccaggg gcgtgcgccg ccccgctcag     480
acaccccccc ggccgcccgc gctcaccggt cccgcaaccg cagccaccgc ctccagcccc     540
gcctagaccg tccgccgctc cccgcccggc gccgcggcgc cccgcgatga cgttgacgcc     600
tcccattggc tgcttgtccg aggcccgacg gactggctgc ccaggggcgg tggccccgcc     660
cccggcccgc cgcgcatcc                                                  679

<210> SEQ ID NO 2
<211> LENGTH: 6462
<212> TYPE: DNA
<213> ORGANISM: Homo sapiens
<220> FEATURE:
<221> NAME/KEY: exon
<222> LOCATION: (1)..(168)
<221> NAME/KEY: intron
<222> LOCATION: (169)..(233)
<221> NAME/KEY: exon
<222> LOCATION: (234)..(267)
<221> NAME/KEY: intron
<222> LOCATION: (268)..(360)
<221> NAME/KEY: exon
<222> LOCATION: (361)..(455)
<221> NAME/KEY: intron
<222> LOCATION: (456)..(678)
<221> NAME/KEY: exon
<222> LOCATION: (679)..(819)
<221> NAME/KEY: intron
<222> LOCATION: (820)..(1104)
<221> NAME/KEY: exon
<222> LOCATION: (1105)..(1881)
<221> NAME/KEY: intron
<222> LOCATION: (1882)..(1978)
<221> NAME/KEY: exon
<222> LOCATION: (1979)..(2105)
<221> NAME/KEY: intron
<222> LOCATION: (2106)..(2411)
<221> NAME/KEY: exon
<222> LOCATION: (2412)..(2543)
<221> NAME/KEY: intron
<222> LOCATION: (2544)..(2626)
<221> NAME/KEY: exon
<222> LOCATION: (2627)..(2719)
<221> NAME/KEY: intron
<222> LOCATION: (2720)..(2796)
<221> NAME/KEY: exon
<222> LOCATION: (2797)..(2933)
<221> NAME/KEY: intron
<222> LOCATION: (2934)..(3343)

-continued

```
<221> NAME/KEY: exon
<222> LOCATION: (3344)..(3427)
<221> NAME/KEY: intron
<222> LOCATION: (3428)..(3506)
<221> NAME/KEY: exon
<222> LOCATION: (3507)..(3680)
<221> NAME/KEY: intron
<222> LOCATION: (3681)..(3761)
<221> NAME/KEY: exon
<222> LOCATION: (3762)..(3941)
<221> NAME/KEY: intron
<222> LOCATION: (3942)..(4043)
<221> NAME/KEY: exon
<222> LOCATION: (4044)..(4185)
<221> NAME/KEY: intron
<222> LOCATION: (4186)..(4275)
<221> NAME/KEY: exon
<222> LOCATION: (4276)..(4538)
<221> NAME/KEY: intron
<222> LOCATION: (4539)..(4615)
<221> NAME/KEY: exon
<222> LOCATION: (4616)..(4907)
<221> NAME/KEY: intron
<222> LOCATION: (4908)..(4982)
<221> NAME/KEY: exon
<222> LOCATION: (4983)..(5112)
<221> NAME/KEY: intron
<222> LOCATION: (5113)..(5192)
<221> NAME/KEY: exon
<222> LOCATION: (5193)..(5362)
<221> NAME/KEY: intron
<222> LOCATION: (5363)..(5429)
<221> NAME/KEY: exon
<222> LOCATION: (5430)..(5610)
<221> NAME/KEY: intron
<222> LOCATION: (5611)..(5686)
<221> NAME/KEY: exon
<222> LOCATION: (5687)..(5843)
<221> NAME/KEY: intron
<222> LOCATION: (5844)..(5964)
<221> NAME/KEY: exon
<222> LOCATION: (5965)..(6073)
<221> NAME/KEY: intron
<222> LOCATION: (6074)..(6198)
<221> NAME/KEY: exon
<222> LOCATION: (6199)..(6462)

<400> SEQUENCE: 2
gcattggctg tcggcccccg cgacggctgc gcgggagatt cgctggacga tcgcaagcgc     60
ggaggccggg cgggcgcgcg cgccatggag cggctgcggg acgtgcggga gcggctgcag    120
gcgtgggagc gcgcgttccg acggcagcgc gggcggcgac cgagccaggt gcgggctgcc    180
caggggccga ggggctgagg gcgcggcccg cggctgacgg gttcccttta caggacgacg    240
tggaggcggc gccggaggag acccgcggtg agcgcgcggc ggggcggcgg gggcgagaag    300
acaccgggtc ggcaggggcc caggccccac cctgaccccg cctcccgctc gcccacgcag    360
cgctctaccg ggagtaccgc actctgaagc gtaccacggg ccaggccggc ggcgggctcc    420
gcagctccga gtcgctcccc gcggcggccg aagaggtacc caggccccgc cgccccagcc    480
tcctcccact tccctgtttg gcggagtggc gggagccacg gagtcgcggc caggcctccg    540
tggggcacag aacttgggag ggggactggg caaagtgaag aagggccggg cctcgctcca    600
ggtgcgggag gggtggctgg gagcgcttct gccgccacaa cagcctttc tggcctgtgc     660
ccctgttgtc tcctgcaggc gccagagccc cgctgctggg ggcccatct gaatcgggct     720
gcgaccaaga gtccacagcc tacgccaggg cggagccgcc agggctcggt gccggactac    780
gggcagcggc tcaaggccaa tctgaaaggc accctgcagg tgaggagtgg gcaggcagtg    840
agtccacgct aggtccacag ctgcttccgg tccgggtcgc cctcttgtca tttttccac    900
```

-continued

| | |
|---|---|
| acagacaggc acgggcccct gtgccaacca gggcacgagt cttcagggag cttctcgggg | 960 |
| ccttcgccct tgactcccctt tctagtccag ccttgtgcta attagcctgc tctacaattg | 1020 |
| agcgtgggga ctcaggtagg ttttagagtc tacagtagct caggggcctg agttcctcct | 1080 |
| gctgttctgc tgttcccctc ccaggccgga ccagccctgg ccgcagacc gtggcctcta | 1140 |
| ggaagagcct catctaaggc atccacccca aagcccccag gtacagggcc tgtcccctcc | 1200 |
| tttgcagaaa aagtcagtga tgagcctcca cagctccctg agcccagcc aaggccaggc | 1260 |
| cggctccagc atctgcaggc atccctgagc cagcggctgg gctccctaga tcctggctgg | 1320 |
| ttacagcgat gtcacagtga ggtcccagat tttctggggg cccccaaagc ctgcaggcct | 1380 |
| gatctaggct cagaggaatc acaacttctg atccctggtg agtcggctgt ccttggtcct | 1440 |
| ggtgctggct cccagggccc agaggcttca gccttccaag aagtcagcat ccgtgtgggg | 1500 |
| agcccccagc ccagcagcag tggaggcgag aagcggagat ggaacgagga gccctgggag | 1560 |
| agccccgcac aggtccagca ggagagcagc caagctggac cccatcgga gggggctggg | 1620 |
| gctgtagcag ttgaggaaga ccctccaggg gaacctgtac aggcacagcc acctcagccc | 1680 |
| tgcagcagcc catcgaaccc caggtaccac ggactcagcc cctccagtca gctagggct | 1740 |
| gggaaggctg agggcacagc ccccctgcac atcttccctc ggctggcccg ccatgacagg | 1800 |
| ggcaattacg tacggctcaa catgaagcag aaacactacg tgcggggccg ggcactccgt | 1860 |
| agcaggctcc tccgcaagca ggtaagacag cgacgggcca ggacaggcat tcccttttccc | 1920 |
| tccctcagc cctcccgtat ttcccgccca gtgaccctcc tatgtgggca ccccccaggc | 1980 |
| atggaagcag aagtggcgga agaaagggga gtgttttggg ggtggtggtg ccacagtcac | 2040 |
| aaccaaggag tcttgtttcc tgaacgagca gttcgatcac tgggcagccc agtgtccccg | 2100 |
| gccaggtgag acatctgccc tggagggtgg gtccggccaa cactgtggag agggcgcagt | 2160 |
| gctcttttgg gggacactta tgttccaagc aacaggcctt ccaggtaccc ctggtccagg | 2220 |
| ccctacccta gctcccctga aggagggtgg cagggacgac gatggctgtc actcttttct | 2280 |
| gctttggaaa aagtagccca gaggaaggc actgcctgct gccaaccccc tttgggggaa | 2340 |
| ggagaggttg tggccagtgg ttgtcttgcc cgacctggag ctcccattct accctctcct | 2400 |
| gcctgcccca gcaagtgagg aagacacaga tgctgttggg cctgagccac tggttccttc | 2460 |
| accacaacct gtacctgagg tgcccagcct ggaccccacc gtgctgccac tctactccct | 2520 |
| ggggccctca gggcagttgg caggtgagca gtcagcttct ggcccagagc cttcactgag | 2580 |
| gggttggggt gactcaagtc atggtgatca acatctgtgt ctgcagagac gccggctgag | 2640 |
| gtgttccagg ccctggagca gctggggcac caagcctttc gccctgggca ggagcgtgca | 2700 |
| gtcatgcgga tcctgtctgg tgagcgtggc tgccagggct gaggctgggc tgaggccagg | 2760 |
| ctgcagaacc ctgctgctga ctcccgcccc atccaggcat ctccacgctg ctggtgctgc | 2820 |
| ctacaggtgc cggcaagtcc ctgtgctacc agctcccagc gctgctctac agccggcgca | 2880 |
| gccccctgcct cacgttggtc gtctctcccc tgctgtcact catggatgac caggtgtgca | 2940 |
| cacagggccc tggcacacg tacacagcca agaaccagca cttgtgactc ccaagggcaa | 3000 |
| ctgctgcttg tccctaacc accccctccc ctgggagctt caaggtgtct gtggcctcag | 3060 |
| tcccagtctt ggcagcaggt caaaggcagc ccagctccac aggcaccaca gccacccccta | 3120 |
| cgggaaatgt gctgggaaag gagccatccc tacttcagtc tgtctgctct ggggctcctg | 3180 |
| ggccaaggcc cacaggtggc tctaaaccct tagccctagg acccaggacc tggttctcct | 3240 |
| ctccccctgag ggactaggat ggacatggca gcagatctgg gatgacttgg ggaagggcca | 3300 |

```
gggctgggct ggcgtatgac ggctgtcgtt cctgcatttg caggtgtctg gcctgccacc    3360
gtgtctcaag gcggcctgca tacactcggg catgaccagg aagcaacggg aatctgtcct    3420
gcagaaggtg ggggcctcat gggcctaggg gtgagggagg cagcgggcgg gcacctgggc    3480
tgtgcctctg atcttgctgc cttcagattc gggcagccca ggtacacgtg ctgatgctga    3540
cacctgaggc actggtgggg gcggaggcc tccctccagc cgcacagctg cctccagttg     3600
cttttgcctg cattgatgag gcccactgcc tctcccagtg gtcccacaac ttccggccct    3660
gctacctgcg cgtctgcaag gtgagccata tgtgaactgg ggtgggcggc cagggccggg    3720
atgggctggg cggcctcaca ccactgccgc tctggtgca ggtgcttcgg gagcgcatgg     3780
gcgtgcactg cttcctgggc ctcacagcca cagccacacg ccgcactgcc agtgacgtgg    3840
cacagcacct ggctgtggct gaagagcctg acctccacgg gccagcccca gttcccacca    3900
acctgcacct ttccgtgtcc atggacaggg acacagacca ggtgggtgtg tgtgctctgg    3960
ggaccctgca gggccctggc tgctgactgc ccacgccgac ccctcctcac tccccactgc    4020
ccacgccaac cgctcctcat caggcactgt tgacgctgct gcaaggcaaa cgttttcaaa    4080
acctcgattc cattatcatt tactgcaacc ggcgcgagga cacagagcgg atcgctgcgc    4140
tcctccgaac ctgcctgcac gcagcctggg tcccagggtc tggaggtgcg catggacag    4200 agctggtgtc cccgtggacc caccttgggc acacatggtc ccatcccact gaccatctgc    4260
ctgtcttccc caaaggtcgt gccccaaaa ccacagccga ggcctaccac gcgggcatgt     4320
gcagccggga acgcggcgg gtacagcgag ccttcatgca gggccagttg cgggtggtgg     4380
tggccacggt ggcctttggg atgggctgg accggccaga tgtgcgggct gtgctgcatc    4440
tggggctgcc cccaagcttc gagagctacg tgcaggccgt gggccgggcc gggcgtgacg    4500
ggcagcctgc ccactgccac ctcttcctgc agccccaggt tggcaccccc cccccacact    4560
gccagtgctc gagcccccag tggtccaccc caccctcatg aaagttgccc tgcagggcga    4620
agacctgcga gagctgcgca gacatgtgca cgccgacagc acggacttcc tggctgtgaa    4680
gaggctggta cagcgcgtgt tcccagcctg cacctgcacc tgcaccaggc cgccctcgga    4740
gcaggaaggg gccgtgggtg gggagaggcc tgtgcccaag taccccctc aagaggctga     4800 gcagcttagc caccaagcag ccccaggacc cagaagggtc tgcatgggcc atgagcgggc    4860
actcccaata cagcttaccg tacaggcttt ggacatgccg gaggagggtg aggaacctgg    4920
ggtaagccac agggg tgtgg aggggctgtc cccgcgtccg ctgagccctg ctctgcccc    4980 agccatcgag actttgctgt gctacctgga gctgcaccca caccactggc tggagctgct    5040
ggcgaccacc tatacccatt gccgtctgaa ctgccctggg ggccctgccc agctccaggc    5100
cctggcccac aggtaagcac gccctgccca gttggagacg aggttggaga atcagggctg    5160
ttggccacat gtccctttt ccctgggcac aggtgtcccc ctttggctgt gtgcttggcc     5220
cagcagctgc ctgaggaccc agggcaaggc agcagctccg tggagtttga catggtcaag    5280
ctggtggact ccatgggctg ggagctggcc tctgtgcggc gggctctctg ccagctgcag    5340
tgggaccacg agcccaggac aggtgcgcct ctccccaccc cacaccgccc tggacgctgc    5400
ctgcctgcat ctgacatgct ttccggcagg tgtgcggcgt gggacagggg tgcttgtgga    5460
gttcagtgag ctgccttcc accttcgcag cccgggggac ctgaccgctg aggagaagga    5520
ccagatatgt gacttcctct atggccgtgt gcaggcccgg gagcgccagg ccctggcccg    5580
tctgcgcaga accttccagg cctttcacag gttgggagga ggtgggcggg gcctgggacc    5640
atccaccctc ccgcagtgat cagctctgac aggctcctcc ccacagcgta gccttcccca    5700
```

-continued

```
gctgcgggcc ctgcctggag cagcaggatg aggagcgcag caccaggctc aaggacctgc      5760
tcggccgcta ctttgaggaa gaggaagggc aggagccggg aggcatggag gacgcacagg      5820
gccccgagcc agggcaggcc agagtgagtg tagtaaggcc aggcagctca tcggggttgc      5880
aggttccctg ggctgcatgg ggcttgctct gtggatgcag tgccacggga gctcagagga      5940
agcctgatgt gcctgtccac acagctccag gattgggagg accaggtccg ctgcgacatc      6000
cgccagttcc tgtccctgag gccagaggag aagttctcca gcagggctgt ggcccgcatc      6060
ttccacggca tcggtgaggc ctgggaggcc ccacccactg caggctgggg ctgggggctg      6120
gggcaggtga ggcctgggag gctccacccg ctgcaggctg ggctggggc tcacggctgt       6180 gtcttggctc caccgtagga agccctgct acccggccca ggtgtacggg caggaccgac       6240
gcttctggag aaaatacctg cacctgagct tccatgccct ggtgggcctg ccacggaag       6300 agctcctgca ggtggcccgc tgactgcact gcattggggg atgtcgggta gagctggggt      6360
tgtcagaggc tagggcagtg actgaggacc tgggcaaaac ctgccacagg gtgtgggaac      6420
gaggaggctc caaaatgcag aataaaaaat gctcactttg tt                         6462
```

<210> SEQ ID NO 3
<211> LENGTH: 3850
<212> TYPE: DNA
<213> ORGANISM: Homo sapiens
<220> FEATURE:
<221> NAME/KEY: CDS
<222> LOCATION: (85)..(3708)

<400> SEQUENCE: 3

```
gcattggctg tcggccccg cgacggctgc gcgggagatt cgctggacga tcgcaagcgc       60
ggaggccggg cgggcgcgcg cgcc atg gag cgg ctg cgg gac gtg cgg gag        111
                           Met Glu Arg Leu Arg Asp Val Arg Glu
                             1               5 cgg ctg cag gcg tgg gag cgc gcg ttc cga cgg cag cgc ggg cgg cga       159
Arg Leu Gln Ala Trp Glu Arg Ala Phe Arg Arg Gln Arg Gly Arg Arg
 10                  15                  20                  25 ccg agc cag gac gac gtg gag gcg gcg ccg gag gag acc cgc gcg ctc       207
Pro Ser Gln Asp Asp Val Glu Ala Ala Pro Glu Glu Thr Arg Ala Leu
                 30                  35                  40 tac cgg gag tac cgc act ctg aag cgt acc acg ggc cag gcc ggc ggc       255
Tyr Arg Glu Tyr Arg Thr Leu Lys Arg Thr Thr Gly Gln Ala Gly Gly
             45                  50                  55 ggg ctc cgc agc tcc gag tcg ctc ccc gcg gcg gcc gaa gag gcg cca       303
Gly Leu Arg Ser Ser Glu Ser Leu Pro Ala Ala Ala Glu Glu Ala Pro
     60                  65                  70 gag ccc cgc tgc tgg ggg ccc cat ctg aat cgg gct gcg acc aag agt       351
Glu Pro Arg Cys Trp Gly Pro His Leu Asn Arg Ala Ala Thr Lys Ser
 75                  80                  85 cca cag cct acg cca ggg cgg agc cgc cag ggc tcg gtg ccg gac tac       399
Pro Gln Pro Thr Pro Gly Arg Ser Arg Gln Gly Ser Val Pro Asp Tyr
                 90                  95                 100                 105 ggg cag cgg ctc aag gcc aat ctg aaa ggc acc ctg cag gcc gga cca       447
Gly Gln Arg Leu Lys Ala Asn Leu Lys Gly Thr Leu Gln Ala Gly Pro
            110                 115                 120 gcc ctg ggc cgc aga ccg tgg cct cta gga aga gcc tca tct aag gca       495
Ala Leu Gly Arg Arg Pro Trp Pro Leu Gly Arg Ala Ser Ser Lys Ala
        125                 130                 135 tcc acc cca aag ccc cca ggt aca ggg cct gtc ccc tcc ttt gca gaa       543
Ser Thr Pro Lys Pro Pro Gly Thr Gly Pro Val Pro Ser Phe Ala Glu
    140                 145                 150
```

```
aaa gtc agt gat gag cct cca cag ctc cct gag ccc cag cca agg cca       591
Lys Val Ser Asp Glu Pro Pro Gln Leu Pro Glu Pro Gln Pro Arg Pro
    155                 160                 165 ggc cgg ctc cag cat ctg cag gca tcc ctg agc cag cgg ctg ggc tcc       639
Gly Arg Leu Gln His Leu Gln Ala Ser Leu Ser Gln Arg Leu Gly Ser
170                 175                 180                 185 cta gat cct ggc tgg tta cag cga tgt cac agt gag gtc cca gat ttt       687
Leu Asp Pro Gly Trp Leu Gln Arg Cys His Ser Glu Val Pro Asp Phe
                190                 195                 200 ctg ggg gcc ccc aaa gcc tgc agg cct gat cta ggc tca gag gaa tca       735
Leu Gly Ala Pro Lys Ala Cys Arg Pro Asp Leu Gly Ser Glu Glu Ser
            205                 210                 215 caa ctt ctg atc cct ggt gag tcg gct gtc ctt ggt cct ggt gct ggc       783
Gln Leu Leu Ile Pro Gly Glu Ser Ala Val Leu Gly Pro Gly Ala Gly
        220                 225                 230 tcc cag ggc cca gag gct tca gcc ttc caa gaa gtc agc atc cgt gtg       831
Ser Gln Gly Pro Glu Ala Ser Ala Phe Gln Glu Val Ser Ile Arg Val
    235                 240                 245 ggg agc ccc cag ccc agc agc agt gga ggc gag aag cgg aga tgg aac       879
Gly Ser Pro Gln Pro Ser Ser Ser Gly Gly Glu Lys Arg Arg Trp Asn
250                 255                 260                 265 gag gag ccc tgg gag agc ccc gca cag gtc cag cag gag agc agc caa       927
Glu Glu Pro Trp Glu Ser Pro Ala Gln Val Gln Gln Glu Ser Ser Gln
                270                 275                 280 gct gga ccc cca tcg gag ggg gct ggg gct gta gca gtt gag gaa gac       975
Ala Gly Pro Pro Ser Glu Gly Ala Gly Ala Val Ala Val Glu Glu Asp
            285                 290                 295 cct cca ggg gaa cct gta cag gca cag cca cct cag ccc tgc agc agc      1023
Pro Pro Gly Glu Pro Val Gln Ala Gln Pro Pro Gln Pro Cys Ser Ser
        300                 305                 310 cca tcg aac ccc agg tac cac gga ctc agc ccc tcc agt caa gct agg      1071
Pro Ser Asn Pro Arg Tyr His Gly Leu Ser Pro Ser Ser Gln Ala Arg
    315                 320                 325 gct ggg aag gct gag ggc aca gcc ccc ctg cac atc ttc cct cgg ctg      1119
Ala Gly Lys Ala Glu Gly Thr Ala Pro Leu His Ile Phe Pro Arg Leu
330                 335                 340                 345 gcc cgc cat gac agg ggc aat tac gta cgg ctc aac atg aag cag aaa      1167
Ala Arg His Asp Arg Gly Asn Tyr Val Arg Leu Asn Met Lys Gln Lys
                350                 355                 360 cac tac gtg cgg ggc cgg gca ctc cgt agc agg ctc ctc cgc aag cag      1215
His Tyr Val Arg Gly Arg Ala Leu Arg Ser Arg Leu Leu Arg Lys Gln
            365                 370                 375 gca tgg aag cag aag tgg cgg aag aaa ggg gag tgt ttt ggg ggt ggt      1263
Ala Trp Lys Gln Lys Trp Arg Lys Lys Gly Glu Cys Phe Gly Gly Gly
        380                 385                 390 ggt gcc aca gtc aca acc aag gag tct tgt ttc ctg aac gag cag ttc      1311
Gly Ala Thr Val Thr Thr Lys Glu Ser Cys Phe Leu Asn Glu Gln Phe
    395                 400                 405 gat cac tgg gca gcc cag tgt ccc cgg cca gca agt gag gaa gac aca      1359
Asp His Trp Ala Ala Gln Cys Pro Arg Pro Ala Ser Glu Glu Asp Thr
410                 415                 420                 425 gat gct gtt ggg cct gag cca ctg gtt cct tca cca caa cct gta cct      1407
Asp Ala Val Gly Pro Glu Pro Leu Val Pro Ser Pro Gln Pro Val Pro
                430                 435                 440 gag gtg ccc agc ctg gac ccc acc gtg ctg cca ctc tac tcc ctg ggg      1455
Glu Val Pro Ser Leu Asp Pro Thr Val Leu Pro Leu Tyr Ser Leu Gly
            445                 450                 455 ccc tca ggg cag ttg gca gag acg ccg gct gag gtg ttc cag gcc ctg      1503
Pro Ser Gly Gln Leu Ala Glu Thr Pro Ala Glu Val Phe Gln Ala Leu
        460                 465                 470
```

-continued

| | |
|---|---|
| gag cag ctg ggg cac caa gcc ttt cgc cct ggg cag gag cgt gca gtc<br>Glu Gln Leu Gly His Gln Ala Phe Arg Pro Gly Gln Glu Arg Ala Val<br>475     480     485 | 1551 |
| atg cgg atc ctg tct ggc atc tcc acg ctg ctg gtg ctg cct aca ggt<br>Met Arg Ile Leu Ser Gly Ile Ser Thr Leu Leu Val Leu Pro Thr Gly<br>490     495     500     505 | 1599 |
| gcc ggc aag tcc ctg tgc tac cag ctc cca gcg ctg ctc tac agc cgg<br>Ala Gly Lys Ser Leu Cys Tyr Gln Leu Pro Ala Leu Leu Tyr Ser Arg<br>510     515     520 | 1647 |
| cgc agc ccc tgc ctc acg ttg gtc gtc tct ccc ctg ctg tca ctc atg<br>Arg Ser Pro Cys Leu Thr Leu Val Val Ser Pro Leu Leu Ser Leu Met<br>525     530     535 | 1695 |
| gat gac cag gtg tct ggc ctg cca ccg tgt ctc aag gcg gcc tgc ata<br>Asp Asp Gln Val Ser Gly Leu Pro Pro Cys Leu Lys Ala Ala Cys Ile<br>540     545     550 | 1743 |
| cac tcg ggc atg acc agg aag caa cgg gaa tct gtc ctg cag aag att<br>His Ser Gly Met Thr Arg Lys Gln Arg Glu Ser Val Leu Gln Lys Ile<br>555     560     565 | 1791 |
| cgg gca gcc cag gta cac gtg ctg atg ctg aca cct gag gca ctg gtg<br>Arg Ala Ala Gln Val His Val Leu Met Leu Thr Pro Glu Ala Leu Val<br>570     575     580     585 | 1839 |
| ggg gcg gga ggc ctc cct cca gcc gca cag ctg cct cca gtt gct ttt<br>Gly Ala Gly Gly Leu Pro Pro Ala Ala Gln Leu Pro Pro Val Ala Phe<br>590     595     600 | 1887 |
| gcc tgc att gat gag gcc cac tgc ctc tcc cag tgg tcc cac aac ttc<br>Ala Cys Ile Asp Glu Ala His Cys Leu Ser Gln Trp Ser His Asn Phe<br>605     610     615 | 1935 |
| cgg ccc tgc tac ctg cgc gtc tgc aag gtg ctt cgg gag cgc atg ggc<br>Arg Pro Cys Tyr Leu Arg Val Cys Lys Val Leu Arg Glu Arg Met Gly<br>620     625     630 | 1983 |
| gtg cac tgc ttc ctg ggc ctc aca gcc aca gcc aca cgc cgc act gcc<br>Val His Cys Phe Leu Gly Leu Thr Ala Thr Ala Thr Arg Arg Thr Ala<br>635     640     645 | 2031 |
| agt gac gtg gca cag cac ctg gct gtg gct gaa gag cct gac ctc cac<br>Ser Asp Val Ala Gln His Leu Ala Val Ala Glu Glu Pro Asp Leu His<br>650     655     660     665 | 2079 |
| ggg cca gcc cca gtt ccc acc aac ctg cac ctt tcc gtg tcc atg gac<br>Gly Pro Ala Pro Val Pro Thr Asn Leu His Leu Ser Val Ser Met Asp<br>670     675     680 | 2127 |
| agg gac aca gac cag gca ctg ttg acg ctg ctg caa ggc aaa cgt ttt<br>Arg Asp Thr Asp Gln Ala Leu Leu Thr Leu Leu Gln Gly Lys Arg Phe<br>685     690     695 | 2175 |
| caa aac ctc gat tcc att atc att tac tgc aac cgg cgc gag gac aca<br>Gln Asn Leu Asp Ser Ile Ile Ile Tyr Cys Asn Arg Arg Glu Asp Thr<br>700     705     710 | 2223 |
| gag cgg atc gct gcg ctc ctc cga acc tgc ctg cac gca gcc tgg gtc<br>Glu Arg Ile Ala Ala Leu Leu Arg Thr Cys Leu His Ala Ala Trp Val<br>715     720     725 | 2271 |
| cca ggg tct gga ggt cgt gcc ccc aaa acc aca gcc gag gcc tac cac<br>Pro Gly Ser Gly Gly Arg Ala Pro Lys Thr Thr Ala Glu Ala Tyr His<br>730     735     740     745 | 2319 |
| gcg ggc atg tgc agc cgg gaa cgg cgg cgg gta cag cga gcc ttc atg<br>Ala Gly Met Cys Ser Arg Glu Arg Arg Arg Val Gln Arg Ala Phe Met<br>750     755     760 | 2367 |
| cag ggc cag ttg cgg gtg gtg gtg gcc acg gtg gcc ttt ggg atg ggg<br>Gln Gly Gln Leu Arg Val Val Val Ala Thr Val Ala Phe Gly Met Gly<br>765     770     775 | 2415 |

-continued

| | | |
|---|---|---|
| ctg gac cgg cca gat gtg cgg gct gtg ctg cat ctg ggg ctg ccc cca<br>Leu Asp Arg Pro Asp Val Arg Ala Val Leu His Leu Gly Leu Pro Pro<br>780                                       785                         790 | 2463 | |
| agc ttc gag agc tac gtg cag gcc gtg ggc cgg gcc ggg cgt gac ggg<br>Ser Phe Glu Ser Tyr Val Gln Ala Val Gly Arg Ala Gly Arg Asp Gly<br>    795                                 800 | 2511 | |
| cag cct gcc cac tgc cac ctc ttc ctg cag ccc cag ggc gaa gac ctg<br>Gln Pro Ala His Cys His Leu Phe Leu Gln Pro Gln Gly Glu Asp Leu<br>810                                       815                         820                         825 | 2559 | |
| cga gag ctg cgc aga cat gtg cac gcc gac agc acg gac ttc ctg gct<br>Arg Glu Leu Arg Arg His Val His Ala Asp Ser Thr Asp Phe Leu Ala<br>                    830                         835                         840 | 2607 | |
| gtg aag agg ctg gta cag cgc gtg ttc cca gcc tgc acc tgc acc tgc<br>Val Lys Arg Leu Val Gln Arg Val Phe Pro Ala Cys Thr Cys Thr Cys<br>845                                       850                         855 | 2655 | |
| acc agg ccg ccc tcg gag cag gaa ggg gcc gtg ggt ggg gag agg cct<br>Thr Arg Pro Pro Ser Glu Gln Glu Gly Ala Val Gly Gly Glu Arg Pro<br>    860                                 865                         870 | 2703 | |
| gtg ccc aag tac ccc cct caa gag gct gag cag ctt agc cac caa gca<br>Val Pro Lys Tyr Pro Pro Gln Glu Ala Glu Gln Leu Ser His Gln Ala<br>875                                       880                         885 | 2751 | |
| gcc cca gga ccc aga agg gtc tgc atg ggc cat gag cgg gca ctc cca<br>Ala Pro Gly Pro Arg Arg Val Cys Met Gly His Glu Arg Ala Leu Pro<br>890                           895                         900                         905 | 2799 | |
| ata cag ctt acc gta cag gct ttg gac atg ccg gag gag gcc atc gag<br>Ile Gln Leu Thr Val Gln Ala Leu Asp Met Pro Glu Glu Ala Ile Glu<br>                    910                         915                         920 | 2847 | |
| act ttg ctg tgc tac ctg gag ctg cac cca cac cac tgg ctg gag ctg<br>Thr Leu Leu Cys Tyr Leu Glu Leu His Pro His His Trp Leu Glu Leu<br>                  925                         930                         935 | 2895 | |
| ctg gcg acc acc tat acc cat tgc cgt ctg aac tgc cct ggg ggc cct<br>Leu Ala Thr Thr Tyr Thr His Cys Arg Leu Asn Cys Pro Gly Gly Pro<br>940                                       945                         950 | 2943 | |
| gcc cag ctc cag gcc ctg gcc cac agg tgt ccc cct ttg gct gtg tgc<br>Ala Gln Leu Gln Ala Leu Ala His Arg Cys Pro Pro Leu Ala Val Cys<br>    955                                 960                         965 | 2991 | |
| ttg gcc cag cag ctg cct gag gac cca ggg caa ggc agc agc tcc gtg<br>Leu Ala Gln Gln Leu Pro Glu Asp Pro Gly Gln Gly Ser Ser Ser Val<br>970                                       975                         980                         985 | 3039 | |
| gag ttt gac atg gtc aag ctg gtg gac tcc atg ggc tgg gag ctg gcc<br>Glu Phe Asp Met Val Lys Leu Val Asp Ser Met Gly Trp Glu Leu Ala<br>                    990                         995                         1000 | 3087 | |
| tct gtg cgg cgg gct ctc tgc cag ctg cag tgg gac cac gag ccc agg<br>Ser Val Arg Arg Ala Leu Cys Gln Leu Gln Trp Asp His Glu Pro Arg<br>                    1005                        1010                        1015 | 3135 | |
| aca ggt gtg cgg cgt ggg aca ggg gtg ctt gtg gag ttc agt gag ctg<br>Thr Gly Val Arg Arg Gly Thr Gly Val Leu Val Glu Phe Ser Glu Leu<br>                  1020                         1025                        1030 | 3183 | |
| gcc ttc cac ctt cgc agc ccg ggg gac ctg acc gct gag gag aag gac<br>Ala Phe His Leu Arg Ser Pro Gly Asp Leu Thr Ala Glu Glu Lys Asp<br>                    1035                         1040                        1045 | 3231 | |
| cag ata tgt gac ttc ctc tat ggc cgt gtg cag gcc cgg gag cgc cag<br>Gln Ile Cys Asp Phe Leu Tyr Gly Arg Val Gln Ala Arg Glu Arg Gln<br>1050                                     1055                         1060                        1065 | 3279 | |
| gcc ctg gcc cgt ctg cgc aga acc ttc cag gcc ttt cac agc gta gcc<br>Ala Leu Ala Arg Leu Arg Arg Thr Phe Gln Ala Phe His Ser Val Ala<br>                    1070                         1075                        1080 | 3327 | |
| ttc ccc agc tgc ggg ccc tgc ctg gag cag cag gat gag gag cgc agc<br>Phe Pro Ser Cys Gly Pro Cys Leu Glu Gln Gln Asp Glu Glu Arg Ser<br>1085                                     1090                         1095 | 3375 | |

-continued

| | |
|---|---|
| acc agg ctc aag gac ctg ctc ggc cgc tac ttt gag gaa gag gaa ggg<br>Thr Arg Leu Lys Asp Leu Leu Gly Arg Tyr Phe Glu Glu Glu Glu Gly<br>     1100                       1105                     1110 | 3423 |
| cag gag ccg gga ggc atg gag gac gca cag ggc ccc gag cca ggg cag<br>Gln Glu Pro Gly Gly Met Glu Asp Ala Gln Gly Pro Glu Pro Gly Gln<br>1115                      1120                     1125 | 3471 |
| gcc aga ctc cag gat tgg gag gac cag gtc cgc tgc gac atc cgc cag<br>Ala Arg Leu Gln Asp Trp Glu Asp Gln Val Arg Cys Asp Ile Arg Gln<br>1130                    1135                     1140                     1145 | 3519 |
| ttc ctg tcc ctg agg cca gag gag aag ttc tcc agc agg gct gtg gcc<br>Phe Leu Ser Leu Arg Pro Glu Glu Lys Phe Ser Ser Arg Ala Val Ala<br>                   1150                     1155                     1160 | 3567 |
| cgc atc ttc cac ggc atc gga agc ccc tgc tac ccg gcc cag gtg tac<br>Arg Ile Phe His Gly Ile Gly Ser Pro Cys Tyr Pro Ala Gln Val Tyr<br>                   1165                     1170                     1175 | 3615 |
| ggg cag gac cga cgc ttc tgg aga aaa tac ctg cac ctg agc ttc cat<br>Gly Gln Asp Arg Arg Phe Trp Arg Lys Tyr Leu His Leu Ser Phe His<br>1180                      1185                     1190 | 3663 |
| gcc ctg gtg ggc ctg gcc acg gaa gag ctc ctg cag gtg gcc cgc<br>Ala Leu Val Gly Leu Ala Thr Glu Glu Leu Leu Gln Val Ala Arg<br>     1195                     1200                     1205 | 3708 |
| tgactgcact gcattggggg atgtcgggta gagctgggt tgtcagaggc tagggcagtg | 3768 |
| actgaggacc tgggcaaaac ctgccacagg gtgtgggaac gaggaggctc caaaatgcag | 3828 |
| aataaaaaat gctcactttg tt | 3850 |

<210> SEQ ID NO 4
<211> LENGTH: 1208
<212> TYPE: PRT
<213> ORGANISM: Homo sapiens

<400> SEQUENCE: 4

Met Glu Arg Leu Arg Asp Val Arg Glu Arg Leu Gln Ala Trp Glu Arg
1               5                   10                  15

Ala Phe Arg Arg Gln Arg Gly Arg Pro Ser Gln Asp Asp Val Glu
        20                  25                  30

Ala Ala Pro Glu Glu Thr Arg Ala Leu Tyr Arg Glu Tyr Arg Thr Leu
    35                  40                  45

Lys Arg Thr Thr Gly Gln Ala Gly Gly Leu Arg Ser Ser Glu Ser
    50                  55                  60

Leu Pro Ala Ala Glu Glu Ala Pro Glu Pro Arg Cys Trp Gly Pro
65                  70                  75                  80

His Leu Asn Arg Ala Ala Thr Lys Ser Pro Gln Pro Thr Pro Gly Arg
                85                  90                  95

Ser Arg Gln Gly Ser Val Pro Asp Tyr Gly Gln Arg Leu Lys Ala Asn
            100                 105                 110

Leu Lys Gly Thr Leu Gln Ala Gly Pro Ala Leu Gly Arg Arg Pro Trp
        115                 120                 125

Pro Leu Gly Arg Ala Ser Ser Lys Ala Ser Thr Pro Lys Pro Pro Gly
    130                 135                 140

Thr Gly Pro Val Pro Ser Phe Ala Glu Lys Val Ser Asp Glu Pro Pro
145                 150                 155                 160

Gln Leu Pro Glu Pro Gln Pro Arg Pro Gly Arg Leu Gln His Leu Gln
                165                 170                 175

Ala Ser Leu Ser Gln Arg Leu Gly Ser Leu Asp Pro Gly Trp Leu Gln
            180                 185                 190

```
Arg Cys His Ser Glu Val Pro Asp Phe Leu Gly Ala Pro Lys Ala Cys
        195                 200                 205

Arg Pro Asp Leu Gly Ser Glu Glu Ser Gln Leu Leu Ile Pro Gly Glu
    210                 215                 220

Ser Ala Val Leu Gly Pro Gly Ala Gly Ser Gln Gly Pro Glu Ala Ser
225                 230                 235                 240

Ala Phe Gln Glu Val Ser Ile Arg Val Gly Ser Pro Gln Pro Ser Ser
                    245                 250                 255

Ser Gly Gly Glu Lys Arg Arg Trp Asn Glu Glu Pro Trp Glu Ser Pro
                260                 265                 270

Ala Gln Val Gln Gln Glu Ser Gln Ala Gly Pro Ser Glu Gly
            275                 280                 285

Ala Gly Ala Val Ala Val Glu Glu Asp Pro Pro Gly Glu Pro Val Gln
290                 295                 300

Ala Gln Pro Pro Gln Pro Cys Ser Ser Pro Ser Asn Pro Arg Tyr His
305                 310                 315                 320

Gly Leu Ser Pro Ser Ser Gln Ala Arg Ala Gly Lys Ala Glu Gly Thr
                325                 330                 335

Ala Pro Leu His Ile Phe Pro Arg Leu Ala Arg His Asp Arg Gly Asn
            340                 345                 350

Tyr Val Arg Leu Asn Met Lys Gln Lys His Tyr Val Arg Gly Arg Ala
        355                 360                 365

Leu Arg Ser Arg Leu Leu Arg Lys Gln Ala Trp Lys Gln Lys Trp Arg
    370                 375                 380

Lys Lys Gly Glu Cys Phe Gly Gly Gly Gly Ala Thr Val Thr Thr Lys
385                 390                 395                 400

Glu Ser Cys Phe Leu Asn Glu Gln Phe Asp His Trp Ala Ala Gln Cys
                    405                 410                 415

Pro Arg Pro Ala Ser Glu Glu Asp Thr Asp Ala Val Gly Pro Glu Pro
                420                 425                 430

Leu Val Pro Ser Pro Gln Pro Val Pro Glu Val Pro Ser Leu Asp Pro
            435                 440                 445

Thr Val Leu Pro Leu Tyr Ser Leu Gly Pro Ser Gly Gln Leu Ala Glu
    450                 455                 460

Thr Pro Ala Glu Val Phe Gln Ala Leu Glu Gln Leu Gly His Gln Ala
465                 470                 475                 480

Phe Arg Pro Gly Gln Glu Arg Ala Val Met Arg Ile Leu Ser Gly Ile
                    485                 490                 495

Ser Thr Leu Leu Val Leu Pro Thr Gly Ala Gly Lys Ser Leu Cys Tyr
                500                 505                 510

Gln Leu Pro Ala Leu Leu Tyr Ser Arg Arg Ser Pro Cys Leu Thr Leu
            515                 520                 525

Val Val Ser Pro Leu Leu Ser Leu Met Asp Asp Gln Val Ser Gly Leu
    530                 535                 540

Pro Pro Cys Leu Lys Ala Ala Cys Ile His Ser Gly Met Thr Arg Lys
545                 550                 555                 560

Gln Arg Glu Ser Val Leu Gln Lys Ile Arg Ala Ala Gln Val His Val
                    565                 570                 575

Leu Met Leu Thr Pro Glu Ala Leu Val Gly Ala Gly Leu Pro Pro
                580                 585                 590

Ala Ala Gln Leu Pro Pro Val Ala Phe Ala Cys Ile Asp Glu Ala His
            595                 600                 605
```

-continued

```
Cys Leu Ser Gln Trp Ser His Asn Phe Arg Pro Cys Tyr Leu Arg Val
    610                 615                 620
Cys Lys Val Leu Arg Glu Arg Met Gly Val His Cys Phe Leu Gly Leu
625                 630                 635                 640
Thr Ala Thr Ala Thr Arg Arg Thr Ala Ser Asp Val Ala Gln His Leu
                645                 650                 655
Ala Val Ala Glu Glu Pro Asp Leu His Gly Pro Ala Pro Val Pro Thr
            660                 665                 670
Asn Leu His Leu Ser Val Ser Met Asp Arg Asp Thr Asp Gln Ala Leu
        675                 680                 685
Leu Thr Leu Leu Gln Gly Lys Arg Phe Gln Asn Leu Asp Ser Ile Ile
    690                 695                 700
Ile Tyr Cys Asn Arg Arg Glu Asp Thr Glu Arg Ile Ala Ala Leu Leu
705                 710                 715                 720
Arg Thr Cys Leu His Ala Ala Trp Val Pro Gly Ser Gly Arg Ala
                725                 730                 735
Pro Lys Thr Thr Ala Glu Ala Tyr His Ala Gly Met Cys Ser Arg Glu
            740                 745                 750
Arg Arg Arg Val Gln Arg Ala Phe Met Gln Gly Gln Leu Arg Val Val
        755                 760                 765
Val Ala Thr Val Ala Phe Gly Met Gly Leu Asp Arg Pro Asp Val Arg
    770                 775                 780
Ala Val Leu His Leu Gly Leu Pro Pro Ser Phe Glu Ser Tyr Val Gln
785                 790                 795                 800
Ala Val Gly Arg Ala Gly Arg Asp Gly Gln Pro Ala His Cys His Leu
                805                 810                 815
Phe Leu Gln Pro Gln Gly Glu Asp Leu Arg Glu Leu Arg Arg His Val
            820                 825                 830
His Ala Asp Ser Thr Asp Phe Leu Ala Val Lys Arg Leu Val Gln Arg
        835                 840                 845
Val Phe Pro Ala Cys Thr Cys Thr Cys Thr Arg Pro Pro Ser Glu Gln
    850                 855                 860
Glu Gly Ala Val Gly Gly Glu Arg Pro Val Pro Lys Tyr Pro Pro Gln
865                 870                 875                 880
Glu Ala Glu Gln Leu Ser His Gln Ala Ala Pro Gly Pro Arg Arg Val
                885                 890                 895
Cys Met Gly His Glu Arg Ala Leu Pro Ile Gln Leu Thr Val Gln Ala
            900                 905                 910
Leu Asp Met Pro Glu Glu Ala Ile Glu Thr Leu Leu Cys Tyr Leu Glu
        915                 920                 925
Leu His Pro His His Trp Leu Glu Leu Leu Ala Thr Thr Tyr Thr His
    930                 935                 940
Cys Arg Leu Asn Cys Pro Gly Pro Ala Gln Leu Gln Ala Leu Ala
945                 950                 955                 960
His Arg Cys Pro Pro Leu Ala Val Cys Leu Ala Gln Gln Leu Pro Glu
                965                 970                 975
Asp Pro Gly Gln Gly Ser Ser Val Glu Phe Asp Met Val Lys Leu
            980                 985                 990
Val Asp Ser Met Gly Trp Glu Leu Ala Ser Val Arg Arg Ala Leu Cys
        995                 1000                1005
Gln Leu Gln Trp Asp His Glu Pro Arg Thr Gly Val Arg Arg Gly Thr
    1010                1015                1020
```

-continued

```
Gly Val Leu Val Glu Phe Ser Glu Leu Ala Phe His Leu Arg Ser Pro
1025                1030                1035                1040

Gly Asp Leu Thr Ala Glu Lys Asp Gln Ile Cys Asp Phe Leu Tyr
            1045                1050                1055

Gly Arg Val Gln Ala Arg Glu Arg Gln Ala Leu Ala Arg Leu Arg Arg
        1060                1065                1070

Thr Phe Gln Ala Phe His Ser Val Ala Phe Pro Ser Cys Gly Pro Cys
    1075                1080                1085

Leu Glu Gln Gln Asp Glu Glu Arg Ser Thr Arg Leu Lys Asp Leu Leu
1090                1095                1100

Gly Arg Tyr Phe Glu Glu Glu Glu Gly Gln Glu Pro Gly Gly Met Glu
1105                1110                1115                1120

Asp Ala Gln Gly Pro Glu Pro Gly Gln Ala Arg Leu Gln Asp Trp Glu
            1125                1130                1135

Asp Gln Val Arg Cys Asp Ile Arg Gln Phe Leu Ser Leu Arg Pro Glu
        1140                1145                1150

Glu Lys Phe Ser Ser Arg Ala Val Ala Arg Ile Phe His Gly Ile Gly
    1155                1160                1165

Ser Pro Cys Tyr Pro Ala Gln Val Tyr Gly Gln Asp Arg Arg Phe Trp
    1170                1175                1180

Arg Lys Tyr Leu His Leu Ser Phe His Ala Leu Val Gly Leu Ala Thr
1185                1190                1195                1200

Glu Glu Leu Leu Gln Val Ala Arg
                1205

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 5
tcacaacttc tgatccctgg tgag                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 6
gagggtcttc ctcaactgct acag                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 7
caatgggagg cgtcaacgtc atcg                                          24
```

```
<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 8
gaggcgaaag agcggagggt ccag                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 9
cgcttctgga gaaatacct gcac                                               24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 10
ttggagcctc ctcgttccca cacc                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 11
gtttcctgaa cgagcagttc gatc                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 12
gctgcctcca gttgcttttg cctg                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence
```

```
<400> SEQUENCE: 13
ttggtcgcag cccgattcag atgg                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 14
tggcccgtgg tacgcttcag agtg                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 15
gacggctgcg cgggagattc gctg                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 16
ctcagcccct ccagtcaagc tagg                                              24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 17
accagtgcct caggtgtcag c                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 18
ggaaatgtgc tgggaaagga g                                                 21

<210> SEQ ID NO 19
<211> LENGTH: 21
<212> TYPE: DNA
<213> ORGANISM: Artificial Sequence
```

```
<220> FEATURE:
<223> OTHER INFORMATION: Description of Artificial Sequence:
      Artificially
      synthesized primer sequence

<400> SEQUENCE: 19
accaagagtc cacagcctac g                                          21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 20
gctccgtgga gtttgacatg g                                          21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 21
agcgcagcac caggctcaag g                                          21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 22
gcactgcttc ctgggcctca cagc                                       24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 23
gggtacagcg agccttcatg cagg                                       24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 24
ctcgattcca ttatcattta ctgc                                       24
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 25
ctgggcagga gcgtgcagtc atgc                                    24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 26 agggagaga cgaccaacgt gagg                                     24

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 27
ttaggatccg gggtgcttgt ggagttcagt g                            31

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 28
ttaggatccc agcttaccgt acaggctttg g                            31

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 29
tcctggctgt gaagaggctg gtac                                    24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

```
<400> SEQUENCE: 30
atcccccaat gcagtgcagt cagc                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 31
aatctgggac ctcactgtga catc                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 32
agggtgcctt tcagattggc cttg                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 33
agattcgctg gacgatcgca agcg                                              24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 34
caggttttgc ccaggtcctc agtc                                              24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 35
gtcactgccc tagcctctga caac                                              24

<210> SEQ ID NO 36
<211> LENGTH: 24
<212> TYPE: DNA
<213> ORGANISM: Artificial Sequence
```

```
<220> FEATURE:
<223> OTHER INFORMATION: Description of Artificial Sequence:
      Artificially
      synthesized primer sequence

<400> SEQUENCE: 36
tcatctaagg catccacccc aaag                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 37
gtttcctgaa cgagcagttc gatc                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 38
ggacacagac caggcactgt tgac                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 39
caggccagac tccaggattg ggag                                              24

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 40
ctcttcacag ccaggaagtc c                                                 21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 41
agagctggtg tccccgtgga c                                                 21
```

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 42
tctggcctgc caccgtgtct c                                             21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 43
tggtcatgcc cgagtgtatg c                                             21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 44
tgggaacacg cgctgtacca g                                             21

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 45
gcctcacacc actgccgcct ctgg                                          24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:
      Artificially
      synthesized primer sequence

<400> SEQUENCE: 46
gacaggcaga tggtcagtgg gatg                                          24
```

GENE CAUSATIVE OF ROTHMUND-THOMSON SYNDROME AND GENE PRODUCT

This is a U.S. National Phase Application Under 35 USC 371 and applicant herewith claims the benefit of priority of PCT/JP00/00233 filed Jan. 19, 2000, which was published under PCT Article 21(2) in Japanese and Application No. JP 11/11218 filed in Japan on Jan. 19, 1999.

TECHNICAL FIELD

The present invention relates to a causative gene of Rothmund-Thomson syndrome, methods for the diagnosis of the disease, and diagnostic agents and therapeutic agents for the disease.

BACKGROUND ART

Rothmund-Thomson syndrome ((RTS); poikiloderma congenital) is a rare autosomal recessive hereditary disease, the pathophysiology and causative gene of which remain unrevealed. In 1868, a German ophthalmologist, August Rothmund, reported for the first time, 10 patients from an isolated village in Bayern showing crisis of poikiloderma at their youth and exhibiting at a high frequency juvenile cataracts (A. Rothmund, Arch. Ophthalmol. 4:159 (1887)). In 1936, an English ophthalmologist, Sidney Thomson, reported 3 patients with very similar poikiloderma (M. S. Thomson, Br. J. Dermatol. 48:221 (1936)). Two of the three had bone abnormality. Today, these two similar clinical cases are recognized as Rothmund-Thomson syndrome (RTS). Many cases in children of a variety of races affected with this disease have been reported worldwide, and previously over 200 cases of Rothmund-Thomson syndrome had been reported by Vennos et al. (E. M. Vennos et al., J. Am. Acad. Dermatol. 27:750 (1992); E. M. Vennos and W. D. James, Dermatol. Clinics. 13:143 (1995)). Although there is much clinical information on the Rothmund-Thomson syndrome, only clinical background is available for the diagnosis and no method for diagnosis at the laboratory level has been established.

Clinical symptoms of Rothmund-Thomson syndrome include anetoderma and telangiectasia associated with mixed hyperchromic and hypochromic regions during neonatal period, juvenile canities and alopecia prematura, juvenile cataracts, lower stature, congenital skeletal abnormality, and increased risk of mesenchymal tumor. Cytogenetic studies have shown that cells derived from patients with Rothmund-Thomson syndrome are genetically unstable and often exhibit chromosomal recombination, and acquired somatic cell mosaicism can be found in suchcells (K. L. Yingetal., J. Med. Genet. 27:258 (1990); V. M. Der Kaloustian et al., Am. J. Med. Genet. 37:336 (1990); K. H. Orstavik et al., J. Med. Genet. 31:570 (1994); M. Miozzo et al., Int. J. Cancer 77:504 (1998), N. M. Lindor et al., Clin. Genet. 49:124 (1996)). Some of the cytogenetic and clinical findings, including genetic instability in patient cells, juvenile retardation of physical growth, skin abnormality, and high risk of tumorigenesis, are very similar to those findings in Werner syndrome and Bloom syndrome.

Both of the causative genes of Werner syndrome and Bloom syndrome (abbreviated as WRN and BLM, respectively) belong to the RecQ DNA helicase family, and have been identified as homologues of the *E. coli* RecQ gene, which encodes the DNA helicase (K. Nakayama et al., Mol. Gen. Genet. 200:266 (1985)). In addition to WRN and BLM, SGS1 from budding yeast (*S. cerevisiae*) and rqh1+ from fission yeast (*S. pombe*) have been identified as eukaryotic homologues of *E. coli* RecQ DNA helicase. Mutations in the SGS1 gene are known to result in frequent homologous recombination and non-homologous recombination in budding yeast (*S. cerevisiae*) cells; likewise, rqh1+ mutations are known to result in frequent recombination in S phase in fission yeast (*S. pombe*) (S. Gangloff et al., Mol. Cell. Biol. 14:8391 (1994); P. M. Watt et al., Cell 81:253 (1995); E. Stewart et al., EMBO J. 16:2682 (1997)).

Since a trisomy mosaicism of chromosome 8 was found in two of the three Rothmund-Thomson syndrome patients examined (N. M. Lindor et al., Clin. Genet. 49:124 (1996)), the causative gene of Rothmund-Thomson syndrome has been deduced to be located on chromosome 8. However, the causative gene has not yet been identified.

DISCLOSURE OF THE INVENTION

An objective of the present invention is to identify the causative gene of Rothmund-Thomson syndrome. In addition, another objective is to provide methods for the diagnosis of the disease as well as diagnostic and therapeutic agents for the disease. The inventors had previously isolated a cDNA corresponding to the RecQ4 helicase gene, belonging to the RecQ helicase gene family (Japanese Patent Application No. Hei 9-200387). The inventors considered the possibility that the RecQ4 helicase gene was the causative gene of Rothmund-Thomson syndrome; they therefore isolated the genomic DNA encoding RecQ4 helicase, and evaluated the presence of mutations in the RecQ4 helicase gene from patients with Rothmund-Thomson syndrome by using primers prepared based on the sequence information. The results showed that three of seven Rothmund-Thomson syndrome patients tested contained complexed heterozygotic mutations in the RecQ4 gene. Two of these patients were brothers, and the respective mutant alleles of the two had been inherited from the patients' family members. Aberrant transcription of RecQ4 was specifically found in cells derived from the patients. This suggested that the mutations in the RecQ4 gene result in genetic instability and are the cause of Rothmund-Thomson syndrome. In other words, the inventors have successfully demonstrated for the first time that the RecQ4 gene is the causative gene of Rothmund-Thomson syndrome.

Further, from this fact, they have found that it is possible to diagnose Rothmund-Thomson syndrome by detecting mutations in the RecQ4 helicase gene; moreover, it is possible to treat the disease by compensating for the mutations.

The present invention relates to the causative gene of Rothmund-Thomson syndrome, methods for the diagnosis of the disease, and diagnostic and therapeutic agents for the disease, and more specifically to:

(1) a genomic DNA encoding RecQ4 helicase;
(2) a vector comprising the genomic DNA of (1);
(3) a host cell containing the vector of (2);
(4) a DNA used for diagnosis of Rothmund-Thomson syndrome, which hybridizes to a DNA encoding the RecQ4 helicase or to the expression regulatory region thereof having a chain length of at least 15 nucleotides,
(5) a therapeutic agent for Rothmund-Thomson syndrome, which contains as the effective ingredient a DNA encoding RecQ4 helicase;
(6) a therapeutic agent for Rothmund-Thomson syndrome, which contains as the effective ingredient RecQ4 helicase;

(7) a diagnostic agent for Rothmund-Thomson syndrome, which contains as the effective ingredient an antibody capable of binding to RecQ4 helicase;
(8) a method for the diagnosis of Rothmund-Thomson syndrome, characterized by detecting mutations in the DNA encoding RecQ4 helicase or the expression regulatory region thereof;
(9) a method for the diagnosis of Rothmund-Thomson syndrome of (8), comprising the steps of:
   (a) preparing DNA samples from patients;
   (b) amplifying the prepared DNA samples by using the DNA of (4) as a primer and determining the base sequence; and
   (c) comparing the determined base sequence with that of a healthy, normal person;
(10) a method for the diagnosis of Rothmund-Thomson syndrome of (8), comprising the steps of:
   (a) preparing RNA samples from patients;
   (b) separating the prepared RNA samples according to their size;
   (c) using the DNA of (4) as a probe, hybridizing it to the separated RNAs; and
   (d) detecting hybridized RNA and comparing the results with that of a healthy, normal person;
(11) a method for the diagnosis of Rothmund-Thomson syndrome of (8), comprising the steps of:
   (a) preparing DNA samples from patients;
   (b) amplifying the prepared DNA samples using the DNA of (4) as a primer;
   (c) dissociating the amplified DNA into single-stranded DNAs;
   (d) fractionating the dissociated single-stranded DNAs on a non-denaturing gel; and
   (e) comparing the mobility of the fractionated single-stranded DNAs on the gel with that of the healthy normal control;
(12) a method for the diagnosis of Rothmund-Thomson syndrome of (8), comprising the steps of:
   (a) preparing DNA samples from patients;
   (b) amplifying the prepared DNA samples using oligonucleotides comprising a base that forms a base pair with the mutated base specific for Rothmund-Thomson syndrome in the DNA encoding RecQ4 helicase, or the expression regulatory region thereof, as at least one of the primers; and
   (c) detecting the amplified DNA fragment;
(13) a method for the diagnosis of Rothmund-Thomson syndrome of (8), comprising the steps of: (a) preparing DNA samples from patients;
   (b) amplifying the prepared DNA samples using a pair of DNA of (4), which is prepared so as to flank the mutated base specific to Rothmund-Thomson syndrome, as the primer;
   (c) hybridizing to the amplified product a pair of oligonucleotides selected from the group of:
      (i) an oligonucleotide synthesized such that the base forming a base pair with the mutated base in the amplified product corresponds to the 3'-terminus, and an oligonucleotide synthesized such that the neighboring (on the 3' side) base to said 3'-terminus corresponds to the 5' terminus;
      (ii) an oligonucleotide synthesized such that the base forming a base pair with the base of a normal healthy person which corresponds to the mutated base in the amplified product corresponds to the 3'-terminus, and an oligonucleotide synthesized such that a neighboring (on the 3' side) base to said 3'-terminus corresponds to the 5'-terminus;
      (iii) an oligonucleotide synthesized such that the base forming a base pair with the mutated base in the amplification product corresponds to the 5'-terminus, and an oligonucleotide synthesized such that the neighboring (on the 5' side) base to said 5'-terminus corresponds to the 3'-terminus;
      (iv) an oligonucleotide synthesized such that the base forming a base pair with the base of a normal healthy person which corresponds to the mutated base in the amplified product corresponds to the 5'-terminus, and an oligonucleotide synthesized such that the neighboring (on the 5' side) base to said 5'-terminus corresponds to the 3' terminus
   (d) ligating the oligonucleotides; and
   (e) detecting the ligated oligonucleotides; and
(14) a method for the diagnosis of Rothmund-Thomson syndrome of (8), comprising the steps of:
   (a) preparing protein sample from patients;
   (b) contacting an antibody against RecQ4 helicase with the prepared protein sample;
   (c) detecting proteins binding to the antibody.

The present invention primarily relates to the causative gene of Rothmund-Thomson syndrome (RTS). The inventors have found that the causative gene of Rothmund-Thomson syndrome encodes human RecQ4 helicase. The base sequences of the genomic DNA encoding RecQ4 helicase determined by the inventors are shown in SEQ ID NO: 1 (expression regulatory region) and SEQ ID NO: 2 (exon and intron regions).

The genomic DNA encoding RecQ4 helicase of the present invention can be obtained by using the entire base sequence described in any of SEQ ID NOs: 1–3, or a part thereof, as a hybridization probe to screen a genomic DNA library. Alternatively the DNA can be amplified and isolated by polymerase chain reaction (PCR) using a genomic DNA or genomic DNA library as the template and using as the primer a part of the base sequence described in SEQ ID NO: 1 or 2.

The genomic DNA of the present invention, as described below, can be used to prepare primers and probes for the diagnosis of Rothmund-Thomson syndrome, to treat Rothmund-Thomson syndrome by gene therapy, and to produce RecQ4 helicase.

The present invention also relates to DNA hybridizing to DNA encoding RecQ4 helicase, or the expression regulatory region thereof, which comprises at least 15 nucleotides and is used for the diagnosis of Rothmund-Thomson syndrome. Preferably, this DNA hybridizes specifically with a DNA encoding RecQ4 helicase or the expression regulatory region thereof.

The term "hybridizing specifically with" herein means that there is no significant cross-hybridization with DNAs or RNAs encoding other proteins under usual hybridization conditions, preferably under stringent hybridization conditions. Such a DNA doesn't have to be completely complementary to the target sequence but is generally at least 70%, preferably at least 80%, and more preferably at least 90% (for example, 95% or more) identical to the target at the base sequence level.

When used as a primer, the oligonucleotide is generally a 15 mer–35 mer, preferably a 20 mer–28 mer.

The primer may be any one of the above, so long as it is capable of amplifying at least a part of the coding region of RecQ4 helicase or a region regulating expression thereof. Such a region includes, for example, the exon region, the intron region, the promoter region and the enhancer region of the RecQ4 helicase gene.

On the other hand, if the oligonucleotide probe is synthetic, it generally consists of at least 15 bases or more. It is possible to use a double-stranded DNA obtained from a clone inserted into a vector, such as plasmid DNA, as a probe, as well as RNA synthesized from the clone by transcription. The region used as a probe can be any region so long as it hybridizes specifically to at least a part of the coding region of RecQ4 helicase or the region regulating expression thereof. Such a region to which the probe hybridizes includes, for example, the exon region, the intron region, the promoter region and the enhancer region of the RecQ4 helicase gene.

Probes such as oligonucleotides, double-stranded DNAs, and RNAs can be used with proper labels. Labeling methods include, for example, end labeling for oligonucleotides, random primer labeling or PCR method for double-stranded DNAs, and in-vitro transcription labeling for RNAs. Compounds useful for labeling include [$\gamma$-$^{32}$P] ATP for end labeling, [$\alpha$-$^{32}$P] dCTP or digoxigenin (DIG)-dUTP for random primer labeling and PCR method, and [$\alpha$-$^{32}$P] CTP or DIG-UTP for in-vitro transcription labeling.

The "diagnosis of Rothmund-Thomson syndrome", in accordance with the present invention, is characterized by the detection of mutations in the RecQ4 helicase gene. The "diagnosis of Rothmund-Thomson syndrome" in accordance with the present invention includes not only testing of patients exhibiting symptoms of Rothmund-Thomson syndrome due to mutations in the RecQ4 helicase gene, but also includes testing to judge whether or not the subjects are potentially affected with Rothmund-Thomson syndrome due to the mutations in the RecQ4 helicase gene.

In addition, "detection of mutations in the RecQ4 helicase gene", in accordance with the present invention, includes both detection at the protein level and detection at the DNA and at the RNA levels.

One embodiment of the diagnostic test method, in accordance with the present invention, is a method for directly determining base sequence of the RecQ4 helicase gene from patients. This method comprises the steps of: (a) preparing DNA samples from patients; (b) amplifying prepared DNA samples derived from patients by using the DNA of the present invention as a primer to determine the base sequence; and (c) comparing the determined base sequence with that of a healthy normal person. Direct determination of base sequence includes direct determination of base sequence of RecQ4 genomic DNA and direct determination of base sequence of RecQ4 cDNA.

When the base sequence of genomic DNA of RecQ4 is intended to be determined directly, the genomic DNA is prepared from patients, and the RecQ4 gene is amplified from the genomic DNA from patients by using a sense primer and an antisense primer specific to the RecQ4 gene. It is preferred that the primers are 20 mer–28 mer in length and that the Tm values thereof are within the range of 65° C.–75° C. in the amplification of the RecQ4 gene. The RecQ4 genomic DNA, amplified using a sense primer and an antisense primer, is preferably 1 kb–1.5 kb in length. It is preferable to design the sense primer and antisense primer so that the 50 bp–100 bp 5' and 3' ends of the RecQ4 genomic DNA fragment to be amplified overlap with other genomic DNA fragments, thereby covering the entire region of about 6.5 kb of RecQ4 genomic DNA. Further, the expression regulatory region of the RecQ4 gene may be amplified and used as a test subject. The base sequence determination of the amplified fragment can be performed, for example, by the PCR-based method of Hattori et al. (Electrophoresis 13, pp560–565 (1992)). Specifically, the reaction is carried out using a PRISM sequencing kit containing fluorescent dideoxy-terminator (Perkin-Elmer), and using specific primers to the fragment of RecQ4 genomic DNA to be amplified. Subsequently, the base sequence is determined by an automatic sequencer from Applied Biosystems (Model ABI 373), and the data is analyzed by an attached Macintosh computer. The judgment on the presence of mutations can be formed, for example, by analyzing the base sequence, as a series of peaks of waveforms with four colors by using analytical software for base sequence such as Sequencing Analysis (Applied Biosystems). That is, mutations can be detected by comparing the series of peaks of waveforms representing base sequence of genomic DNA of the normal RecQ4 gene with the series of peaks of waveforms representing base sequence of genomic DNA of a patient's RecQ4 gene. Further, the judgment can be formed through sequence analysis, using base sequence-editing software such as DNASIS. In other words, mutations can be detected by comparing the sequence of normal RecQ4 genomic DNA with the sequence of genomic DNA RecQ4 from patients with a computer.

In the case where the base sequence of RecQ4 cDNA is determined directly, the cDNA is prepared from the RNA sample of patients by reverse transcription, and then the RecQ4 gene is amplified from patients using the sense primer and the antisense primer specific to the RecQ4 gene. It is preferable that the primers are 20 mer–28 mer in length and the Tm values thereof are within the range of 65° C.–75° C. in the amplification of the RecQ4 gene. The RecQ4 cDNA amplified using the sense primer and antisense primer is preferably 1 kb–1.5 kb in length. It is preferable to design the sense primer and antisense primer such that the 50 bp–100 bp of 5' and 3' ends of the RecQ4 genomic DNA fragment to be amplified overlap with other genomic DNA fragments, and cover the entire region of RecQ4 cDNA which is about 4 kb. The base sequence determination of the amplified fragment can be performed in the same manner as described above for genomic DNA, for example, by the PCR-based method of Hattori et al. (Electrophoresis 13, pp560–565 (1992)). Specifically, the reaction is carried out using a PRISM sequencing kit containing fluorescent dideoxy-terminator (Perkin-Elmer); in which specific primers are used to the fragment of RecQ4 cDNA to be amplified. Subsequently, the base sequence is determined by an automatic sequencer from Applied Biosystems (Model ABI 373), and the data is analyzed by an attached Macintosh computer. The judgment on the presence of mutations can be formed, for example, by analyzing the base sequence as a series of peaks of waveforms with four colors by using analytical software for base sequence such as Sequencing Analysis (Applied Biosystems). That is, mutations can be detected by comparing the series of peaks of waveforms representing the base sequence of genomic DNA of the normal RecQ4 gene with the series of peaks of waveforms representing the base sequence of genomic DNA of the patients' RecQ4 gene. Further, the judgment can be formed through sequence analysis, using sequence-editing software such as DNASIS. In other words, mutations can be detected by comparing the cDNA sequence of normal RecQ4 with the cDNA sequence of RecQ4 from patients with a computer.

The method for the diagnosis of the present invention includes a variety of other methods in addition to the direct determination method for the base sequence derived from patients as described above. In one embodiment, such a method comprises the steps of: (a) preparing DNA samples from patients; (b) amplifying the prepared DNA samples derived from patients using the DNA of the present invention as a primer; (c) dissociating the amplified DNA into single-stranded DNAs; (d) fractionating the dissociated single-stranded DNAs on a non-denaturing gel; and (e) comparing the mobility of the dissociated single-stranded DNAs on the gel with that of the DNAs from a healthy normal person.

Such a method includes the method of PCR-SSCP (single-strand conformation polymorphism). The PCR-SSCP method is designed based on the principle that two single-stranded DNAs, of which lengths are identical but which base sequences are different, form distinct higher-order structures through their respective intramolecular interactions and therefore show different electrophoretic motilities to each other. That is, the higher-order structure of a single-stranded DNA with a mutation(s) is different from that of a single-stranded DNA without mutation(s), and thus the two exhibit different electrophoretic motilities on a non-denaturing gel. This difference makes it possible to detect the mutation(s) (Orita et al., Proc. Natl. Acad. Sci. USA, 1989, vol. 86, pp2766–pp2770).

The PCR-SSCP method can be used to detect alterations in the sequence of RecQ4 genomic DNA or RecQ4 cDNA. When mutations are intended to be detected in RecQ4 genomic DNA, the RecQ4 gene is amplified from each of the genomic DNAs of healthy normal person and patient, using a sense primer and an antisense primer specific to the RecQ4 gene. In this experiment, the primers are previously radiolabeled with $^{32}$P by an end labeling method. It is preferred that the length of primer is 20 mer–28 mer and the Tm value is within the rage of 65° C.–75° C. Further, it is preferable that the RecQ4 genomic DNA to be amplified, using the sense primer and antisense primer, is 300 bp or shorter in length. Preferably, the sense primer and the antisense primer are designed so that the 60 bp–100 bp of 5' and 3' ends of the RecQ4 genomic DNA fragment to be amplified overlap with other genomic DNA fragments, and cover the entire region of RecQ4 genomic DNA, which is about 6.5 kb. The amplified DNA fragment is electrophoresed on a 5% non-denaturing polyacrylamide the thickness and the length of which is 0.3 mm–0.35 mm and 40 cm, respectively. The gel is analyzed by autoradiography and the mobility of the band from the patient is compared with that from a healthy normal person for detection of mutations.

When mutations are intended to be detected in RecQ4 cDNA, the cDNA is prepared from a patient's RNA sample by reverse transcription, and the RecQ4 gene is amplified from cDNAs of healthy normal person and patient using a sense primer and an antisense primer specific to the RecQ4 gene. In this experiment, the primers are previously radiolabeled with $^{32}$P by an end labeling method. It is preferred that the length of primer is 20 mer–28 mer and the Tm value is within the rage of 65° C.–75° C. Further, it is preferred that the RecQ4 cDNA to be amplified using the sense primer and antisense primer is 300 bp or shorter in length. Preferably the sense primer and antisense primer are designed so that the 60 bp–100 bp of 5' and 3' ends of the RecQ4 cDNA fragment to be amplified overlap with other cDNA fragments and cover the entire region of RecQ4 cDNA which is about 4 kb. The amplified DNA fragment is electrophoresed on a 5% non-denaturing polyacrylamide the thickness and the length of which is 0.3 mm–0.35 mm and 40 cm, respectively. The gel is analyzes by autoradiography and the mobility of the band from the patient is compared with that from a healthy normal person for detection of mutations.

The above-described methods for diagnosis are just a few specific examples and those skilled in the art may properly modify the detailed procedures of the methods. In a test of the genomic DNA, the presence of mutations can be tested in the expression regulatory region (promoter region and enhancer region). Moreover, to test if a particular region of genomic DNA or cDNA has a mutation, a DNA fragment containing the site to be tested may be prepared and used for the test instead of a DNA covering the entire region of the RecQ4 gene.

Alternatively, RNA, instead of DNA prepared from patients, can also be used for the detection. Such a method comprises the steps of: (a) preparing RNA samples from patients; (b) separating the prepared RNA samples based on their size; (c) allowing the DNA probe of the present invention, which has been detectably labeled, to hybridize with the separated RNA; and (d) detecting the hybridized RNA and comparing the RNA with that from a healthy normal person. In a specific example, the RNA prepared from patients is electrophoresed, and Northern blotting is performed using the probe DNA of the present invention to detect the presence and intensity of the signal, and/or the difference in mobility on a gel.

In addition to these methods, it is possible to perform the test of the present invention by detecting mutations at positions selected previously.

One embodiment of such a test method comprises the steps of: (a) preparing DNA samples from patients; (b) amplifying the prepared DNA samples from patients using an oligonucleotide containing a base capable of forming a base pair with the mutated base specific for Rothmund-Thomson syndrome in the DNA encoding RecQ4 helicase or the expression regulatory region thereof as at least one of the primers; and (c) detecting the amplified DNA fragment.

Such a method includes, for example, the method of MASA (mutant-allele-specific amplification) (Matsumoto et al., Experimental Medicine 15:2211–2217 (1977); Unexamined Published Japanese Patent Application (JP-A) No. Hei 10-201498).

MASA is a method in which template genomic DNA or cDNA is amplified by polymerase chain reaction (PCR) using oligonucleotides containing bases capable of forming a base pair with the mutated base as one of the primers, and subsequently subjecting them to gel electrophoresis to detect the mutant alleles.

To conduct this method in accordance with the present invention, a pair of primers (5'-side sense primer and 3'-side antisense primer) is synthesized to amplify the template DNA. Herein, the 5'-side sense primer is synthesized so as to contain a base capable of forming a base pair with the mutated base. The 5'-side sense primer is designed so as to function as a specific primer when a mutation-containing DNA encoding RecQ4 helicase or the expression regulatory region thereof is used as a template, but not when a mutation-free DNA encoding RecQ4 helicase or the expression regulatory region thereof is used. In this case, it is preferred that the base forming a base pair with the mutated base is placed at the 3' end of the 5'-side sense primer. On the other hand, an oligonucleotide primer specifically hybridizing to the region without a mutation is used as the 3'-side sense primer. Polymerase chain reaction is carried out under a condition where the amplification is very efficient, due to the efficient hybridization of the 5'-side sense primer to the template of mutation-containing DNA fragment (abnormal allele), and where the efficiency of amplification is extremely low, due to the incompetence of the 5'-side sense primer in the hybridization to the template of mutation-free DNA fragment (normal allele).

For example, heating once at 95° C. for 5 minutes; heating at 94° C. for 30 seconds, heating at 50° C. for 30 seconds and heating at 72° C. for 30 seconds as one cycle, and that for 40 cycles; and a heating at 72° C. for 4 minutes are carried out.

Alternatively, polymerase chain reaction can be performed in the same manner, using a 3'-side antisense primer containing a base forming a base pair with the mutated base and a 5'-side sense primer that is an oligonucleotide specifically hybridizing to the region without a mutation.

Thus mutation-containing sample DNA can be amplified efficiently because the DNA can hybridize to the mutation-containing primer. For example, when the amplified DNA is subjected to electrophoresis, it can be detected as a positive band on the gel. On the other hand, sample DNA from a normal subject is incompetent in the hybridization with a primer containing the mutation and as a result the amplification is not achieved and no band is observed on the gel.

Further, in addition to the detection with the above-mentioned mutation-containing primer, another detection can be carried out using a primer without the mutation (which contains a base incapable of forming a base pair with the mutated base but capable of forming a base pair with the normal base) corresponding to the primer above, to judge whether the subject has the mutation homozygously or heterozygously. That is, when a band is detected with the mutation-containing primer and no band is detected with the mutation-free primer, then the sample DNA can be judged to have the homozygous mutation associated with Rothmund-Thomson syndrome. Alternatively, when a band is observed with both of the two primers, then the sample DNA can be judged to have the mutation heterozygously, or when a band is detected merely with the primer without the mutation, then the DNA can be judged as normal in respect to the tested site.

Another embodiment of the method for diagnosis of the present invention comprises the steps of: (a) preparing DNA samples from patients; (b) amplifying the prepared DNA samples from patients using oligonucleotides prepared as a pair to flank a mutated base specific to Rothmund-Thomson syndrome as a primer; (c) hybridizing to the obtained amplification product any pair of the oligonucleotides of: (i) an oligonucleotide synthesized such that the 3'-terminus thereof corresponds to the base forming a base pair with the mutated base in the amplification product, and an oligonucleotide synthesized such that the neighboring base (on the 3' side) to said 3'-terminus is placed at the 5'-terminus of the synthesized oligonucleotide; (ii) an oligonucleotide synthesized such that the 3'-terminus thereof corresponds to the base forming a base pair with the base from a healthy normal person corresponding to a mutated nucleotide in the amplification product, and an oligonucleotide synthesized such that the neighboring base (on the 3' side) to said 3'-terminus is placed at the 5'-terminus of the synthesized oligonucleotide; (iii) an oligonucleotide synthesized such that the 5'-terminus thereof corresponds to a base forming a base pair with the mutated base in the amplification product, and an oligonucleotide synthesized such that the neighboring base (on the 5' side) to the 5'-terminus is placed at the 3'-terminus of the synthesized oligonucleotide; (iv) an oligonucleotide synthesized such that the 5'-terminus thereof corresponds to a base forming a base pair with the base from patients corresponding to the mutated base in the amplification product, and an oligonucleotide synthesized such that the neighboring base (on the 5' side) to the 3'-terminus is placed at the 5'-terminus of the synthesized oligonucleotide; ligating these oligonucleotides; and (d) detecting the ligated oligonucleotides.

Such a detection method includes, for example, OLA (Oligonucleotide Ligation Assay) (Matsumoto et al., Experimental Medicine 15:2211–2217 (1977); JP-A No. Hei 10-201498). First, primers are designed to be placed upstream and downstream of each site to be detected (i.e., sites predicted to contain a mutation) with an appropriate spacing, and then polymerase chain reaction is conducted to amplify genomic DNA fragment or cDNA fragment containing the site to be detected. The distance between each site to be detected and the primer can be selected arbitrarily, but 100 bp–200 bp is preferred. Further, there is no particular limitation on the number of nucleotides in the primer, but a primer of 20 mer–30 mer is preferred.

On the other hand, based on the base sequence of the RecQ4 helicase gene, an oligonucleotide consisting of 18–30 nucleotides is synthesized so that the above-mentioned site to be detected is placed at the 3' end thereof and that a base forming a base pair with the predicted mutated base is placed at the 3' end (the synthesized oligonucleotide is referred to as "oligonucleotide A"). Further, another oligonucleotide consisting of 18–30 nucleotides is synthesized so that the base neighboring (on the 3' side) to the above-mentioned site to be detected corresponds to the 5' end thereof (the synthesized oligonucleotide is referred to as "oligonucleotide X"). The mutant-type primer can be prepared by mutagenizing the normal sequence using known technique (e.g., by using a mutagenesis kit (In vitro Mutagenesis Kit, TaKaRa Shuzo)), or alternatively chemically synthesizing the primer based on the sequence designed with a mutation.

According to this preparation, for the convenience of purification and detection of the oligonucleotides ligated through the ligase reaction as described below, it is preferable, for example, to label the 5' end of oligonucleotide A with biotin or the like, to label the 3' end of oligonucleotide X with digoxigenin-11-dideoxy UTP or the like, and to add a phosphate group to the 5' end.

Then, oligonucleotides A and X are annealed with the above-mentioned product of polymerase chain reaction to ligate oligonucleotides A and X with each other. When a mutation of interest is present in the sample DNA, the 3'-end of oligonucleotide A can form a base pair with the mutated base and as a result oligonucleotide A can be connected to oligonucleotide X; and this allows the production of oligonucleotides with labels at both ends (for example, biotin and digoxigenin).

For example, if the product has biotin and digoxigenin at either ends, then the mutation is detected from an arising color reaction, stemming from the absorbance of the product on a plate coated with streptavidin and the subsequent reaction with an anti-digoxigenin antibody conjugated with alkaline phosphatase or the like.

On the contrary, when the sample DNA does not contain the mutation, then the 3'-end of oligonucleotide A cannot form a base pair with the corresponding base in the template DNA, and as a consequence, oligonucleotides A and X cannot be connected with each other.

Accordingly, even when oligonucleotides A and X are labeled, for example, with biotin and digoxigenin, respectively, oligonucleotides with respective labels at respective ends are not formed; and thus even when the ligation reaction product is bound to the plate coated with avidin and the anti-digoxigenin antibody conjugated with alkaline phosphatase or the like is allowed to react thereto, no color reaction is detectable (Delahunty et al., Am. J. Hum. Genet. 58: 1239–1246,1996).

Further, when an oligonucleotide as described below, specifically detecting DNA that doesn't contain mutations at the site to be tested for detection is used, it is possible to judge whether or not the subject has the mutation homozygously. Specifically, an oligonucleotide containing the normal sequence, that has no mutated nucleotide at the above-mentioned site to be detected (which is referred to as oligonucleotide B), is synthesized in the same manner as oligonucleotide A and then the ligation assay between oligonucleotide B and oligonucleotide X is performed in addition to the ligation assay with oligonucleotide A and oligonucleotide X.

If the experimental result shows a positive color reaction with oligonucleotides A and X but not with oligonucleotides B and X, the sample DNA can be judged to have a homozygous mutation associated with Rothmund-Thomson syndrome. Alternatively, when color development is detected in either assays with oligonucleotides A and X and with oligonucleotide B and X, the DNA can be judged to have a heterozygous mutation; when the color reaction is positive in the assay with oligonucleotides B and X alone, the DNA is judged normal at the tested site.

Alternatively, the mutation can be detected in the same manner as with the above-mentioned oligonucleotides A and X, by the combined use of an oligonucleotide in which a base forming a base pair with the predicted mutated base has been introduced at the 5' end and an oligonucleotide prepared such, so that the base flanking (on the 5' side) to the above-mentioned site to be detected corresponds to the 3' end thereof.

The detection method of the present invention can also be conducted by using antibody capable of binding to RecQ4 helicase. In one embodiment, such a method comprises the steps of: (a) preparing protein sample from patients; (b) contacting antibody against RecQ4 helicase with the prepared protein; and (c) detecting a protein binding to the antibody.

The antibody to be used in the test of the present invention may be a monoclonal antibody or a polyclonal antibody. Antibodies binding to RecQ4 helicase can be prepared by a method known to those skilled in the art (see, for example, Japanese Patent Application No. Hei 9-200387). The antigens utilized to prepare antibodies can be provided, for example, by introducing the gene encoding the antigen into an appropriate plasmid vector and expressing the gene product in *E. coli* or, alternatively, by introducing the gene into a baculovirus vector and expressing the gene product in insect cells. Alternatively, a synthetic peptide can also be used. The expression vector can be, for example, a vector such as pQE30 (Qiagen) in the case of *E. coli* expression, or a baculovirus vector such as pAcHLT-B (PharMingen). In this case, the purification of the gene product can be simplified by attaching a tag, such as Flag (Chiang, C. et al., EMBO J., 12: 2749–2762 (1993)) or 6xhis (Immunol. Meth. 4: 121–152 (1990)), to the product. The expressed gene product can be purified utilizing the tag.

A number of cases have been discovered where a protein, which has a truncation at the C terminus of the normal RecQ4 helicase, is presumed to be produced by frame shift or a newly generated termination codon due to mutations in the RecQ4 helicase gene in patients with Rothmund-Thomson syndrome (see Examples). Accordingly, it is possible to carry out easily and efficiently the diagnosis of Rothmund-Thomson syndrome by using antibody recognizing the C terminus of RecQ4 helicase (see Japanese Patent Application No. Hei 10-311284).

In addition, when another antibody recognizing the N terminal region of RecQ4 helicase is used in conjunction with the antibody recognizing the C terminal region in the test of the present invention, it is possible to test which of the two, namely an aberrant expression or structural abnormality of the causative gene, is the cause of the disease associated with mutations of the RecQ4 helicase gene in patients. That is, it is believed that when mutations are generated in the causative gene of the disease, caused by the mutation of the RecQ4 helicase, translation products without the normal C terminus are apt to be produced, due to the resulting frame shift and generation of a termination codon. Therefore, mutations are considered to occur frequently in the C terminal region while the N terminal region is normal. Thus, there is a high possibility that the translation product from the causative gene is detectable by antibody against the N terminal region but not by antibody against the C terminus region when there is a structure abnormality in the translation product.

Furthermore, for example, it has been known that, in the WRN helicase gene, the expression level of mRNA corresponding to the gene containing a mutation(s) is markedly reduced (Yamabe, Y. et al., Biochem. Biophys. Res. Commun., 236: 151–154 (1997)). In the RecQ4 helicase gene, the level of mRNA corresponding to the gene was indeed significantly reduced in RTS patients (see Examples). In such cases, it can be expected that the translation product per se from the RecQ4 helicase gene containing mutations is sometimes undetectable. In such aberrant expression of the RecQ4 helicase gene (marked reduction of the expression), it is expected that no immunological reaction is detectable by any antibody. Accordingly, the diagnosis of Rothmund-Thomson syndrome can be conducted by the combined use of these two antibodies.

The test, using antibody binding to RecQ4 helicase of the present invention, can be conducted utilizing a variety of publicly known immunological techniques. A preferred method is Western blotting. Specifically, cells from a patient are lysed in a buffer containing detergent, the resulting sample is electrophoresed on an SDS polyacrylamide gel (SDS-PAGE) containing sodium dodecyl sulfate (SDS), the proteins are transferred onto a filter from the gel, the protein of interest can be detected on the filter by using antibody binding to RecQ4 helicase. It is also possible to detect RecQ4 helicase by ELISA (enzyme-linked immunosorbent assay, ELISA; I. Roitt et al., In "Immunology", The C. V. Mosby Co., 1989, pp25.5–25.6) or by immunohistochemical staining on tissue sections. The antibody can be labeled, for example, with an enzyme label such as alkaline phosphatase or horseradish peroxidase. In this case, the protein of interest can be detected through color reaction. In addition, a fluorescent label can be also utilized. The label can also be linked to a secondary antibody recognizing the antibody against the protein of interest for the detection of the protein of interest. Alternatively, the label can also be linked to the antibody against the protein of interest for the detection. By utilizing the above-mentioned method, it is possible to conduct the test for the lack, accumulation or abnormal cellular distribution of RecQ4 helicase.

Thus, the antibody binding to RecQ4 helicase can be used in the diagnosis of Rothmund-Thomson syndrome. When used as a diagnostic agent, the antibody is generally used in a buffer of about pH6–pH8 (for example, phosphate buffer, HEPES buffer, or Tris buffer), and if required, it can be mixed with a carrier (for example, bovine serum albumin of about 1–5% or gelatin of about 0.2%), a preservative (for example, 0.1% sodium azide), and so on.

Samples from patients used in the diagnosis of the present invention can be, if it is a test of genomic DNA, any cells containing genomic DNA derived from patients, and, if it is a test of RNA, cDNA or protein, in principle any cells can be used as far as the cells are derived from the patient and correspond to cells expressing the RecQ4 helicase gene in a healthy normal person. For example, it is possible to use fibroblast cells established from a piece of skin tissue obtained by biopsy, cells prepared by transforming B lymphocytes contained in leukocytes obtained by blood collection by using Epstein-Barr virus, or the like.

The present invention further relates to a therapeutic agent for Rothmund-Thomson syndrome. In one embodiment, such a therapeutic agent comprises a DNA encoding RecQ4 helicase as the effective ingredient. If a DNA encoding RecQ4 helicase is used as the therapeutic agent, full-length genomic DNA encoding RecQ4 helicase or a part thereof, or full-length RecQ4 helicase cDNA (cDNA encoding human RecQ4 helicase is shown in SEQ ID NO: 3) or a part thereof is introduced into an appropriate vector, such as adenoviral vector, retroviral vector, or the like, and then, the resulting DNA is administered intravenously or locally to the diseased site to the patient. The administration method can include an ex-vivo method as well as in-vivo method.

Thus, the RecQ4 helicase gene containing the mutations can be replaced with the normal gene in the patient, or alternatively the normal gene can be administered to the patient in an additional fashion, thereby treating Rothmund-Thomson syndrome.

In another embodiment associated with the therapeutic agent for Rothmund-Thomson syndrome, RecQ4 helicase is used as an active ingredient. RecQ4 helicase can be prepared as a naturally occurring protein, or as a recombinant protein provided by genetic recombination techniques. The amino acid sequence of human RecQ4 helicase is shown in SEQ ID NO: 4. The naturally occurring protein can be isolated from tissues or cells highly expressing RecQ4 helicase (for example, thymus and testis, chronic myelogenous leukemia K562 cell, promyelocytic leukemia HL-60 cells, HeLa cell) by a method well known to those skilled in the art, for example, affinity chromatography using antibody against RecQ4 helicase. On the other hand, it is possible to prepare the recombinant protein, for example, through culturing cells transformed with DNA encoding RecQ4 helicase (for example, SEQ ID NO: 3). Cells used for the production of the recombinant protein include mammalian cells, insect cells, yeast cells, and *E. coli*. The expression vectors to be used are known to those skilled in the art. Introduction of the vector into host cells and purification of the recombination protein from the resulting transformants can be achieved by using methods known to those skilled in the art. When it is intended to use the obtained RecQ4 helicase as the therapeutic agent for Rothmund-Thomson syndrome, the RecQ4 helicase can be administered directly or alternatively administered after formulating the RecQ4 helicase by a publicly known pharmaceutical production method. For example, the protein can be administered by dissolving the protein into a commonly used pharmaceutical medium, e.g., a neutral solution such as PBS. The dosage depends on various factors, such as the patient's body weight, age, health, and the type of administration, method to be used. Those skilled in the art can properly select a suitable dosage. The administration can be performed, for example, subcutaneously, orally, directly to the disease site, etc.

In another embodiment associated with the therapeutic agent for Rothmund-Thomson syndrome, the agent comprises compound capable of stimulating and elevating the expression of RecQ4 helicase as the effective ingredient.

There is the possibility that the onset of Rothmund-Thomson syndrome is closely associated with the reduction of the expression level of the RecQ4 helicase gene. Accordingly, stimulating and elevating the expression of the RecQ4 helicase gene may treat Rothmund-Thomson syndrome.

A compound capable of stimulating and elevating the expression of the RecQ4 helicase gene can be obtained by inserting the regulatory region (promoter region and enhancer region) responsible for the expression of the RecQ4 helicase gene into a vector containing luciferase as a reporter, introducing the resulting DNA construct into cultured cells, and screening the cells with the introduced DNA for the compound stimulating and elevating the luciferase activity. The base sequence of the expression regulatory region of the human RecQ4 helicase gene is shown in SEQ ID NO: 1. A reporter gene that can be used for this purpose includes the luciferase gene from firefly and the luciferase gene from *Renilla*. Vectors containing these reporter genes include firefly luciferase reporter vector pGL3 and *Renilla* luciferase reporter vector pRL (Promega). The cells to which the DNA is introduced include human 293 cell, HeLa cell, K562 cell and monkey COS7 cell. Using a publicly known method, such as calcium phosphate precipitation method, liposome method, and electroporation method, introduction of the DNA into cells can be performed. When the method is conducted in accordance with the present invention, the reporter gene connected with the promoter region of the human RecQ4 helicase gene is introduced into human or monkey culture cells by the methods as described above and then the cells are cultured. Each of the various types of sample to be tested are added to the culture medium during the culture and then cell extract is prepared 48 hours after the addition of the compound; the luciferase activity in a cell extract is detected by a method as describe in a reference (Yamabe et al., Mol. Cell. Biol., 1998, vol. 18, pp6191–pp6200). Compounds capable of stimulating and elevating the expression of the RecQ4 helicase gene can be identified through the procedures described above. The sample to be tested in the screening includes., for example, cell extract, expression products from gene library, low-molecular-weight synthetic compound, synthetic peptide, natural compound, etc., but is not limited to these examples.

As with the case of the above-mentioned RecQ4 helicase used as a therapeutic agent, when a compound stimulating and elevating the expression of the RecQ4 helicase gene is used as a therapeutic agent for the disease, it can be administered after formulating the compound by a publicly known pharmaceutical production method.

(a) shows base sequences of the region comprising mut-1 (residue 1641–1672 in the protein-coding region) in normal and mutant RecQ4 genes. The region encircled by mut-1 (7-base deletion) was amplified by PCR using genomic DNAs prepared from a healthy normal person and patients II.2 and II.6 with Rothmund-Thomson syndrome, to analyze the base sequences. The results of sequencing of normal and mutant sequences are indicated below.

(b) shows base sequences of the region comprising mut-2 (residue 2257–2280 of the protein-coding region) in normal and mutant RecQ4 genes. The region encircled by mut-2 (point mutation from C to T) was amplified by PCR using genomic DNAs prepared from a healthy normal person and patients II.2 and II.6 with Rothmund-Thomson syndrome. The sequencing analysis was carried out in the same manner as in (a).

Figure 3:
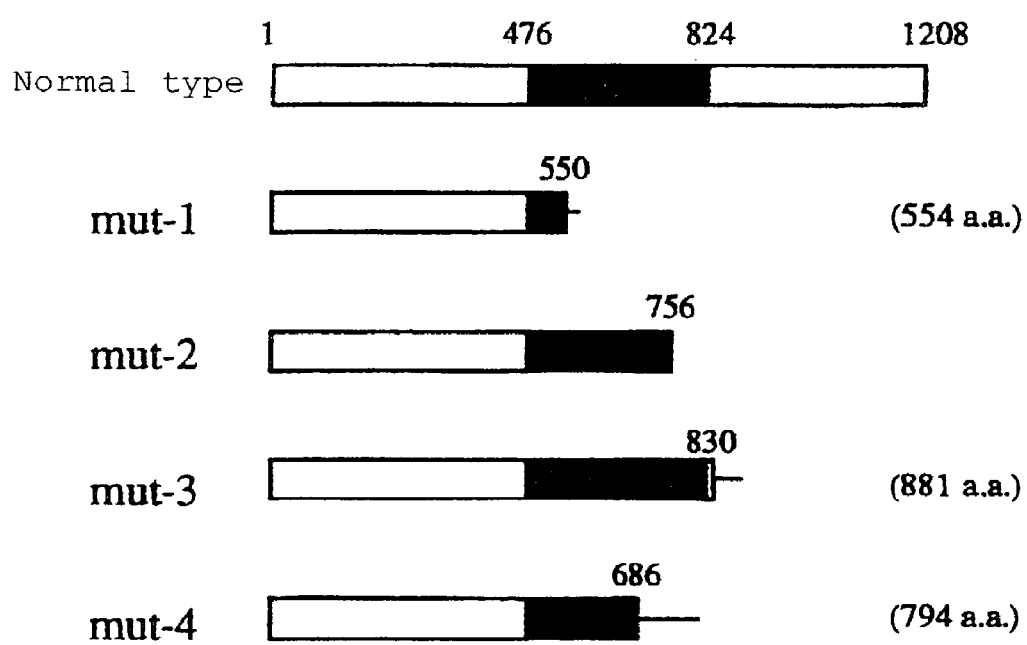

FIG. 3 shows a schematic illustration of deleted RecQ4 helicase molecules generated by mut-1 to mut-4. The term "normal" represents the full-length RecQ4 helicase, consisting of the 1208 amino acids deduced from the coding region of the cloned RecQ4 gene. The shaded region represents a helicase domain that is conserved in all RecQ helicases.

Figure 4:
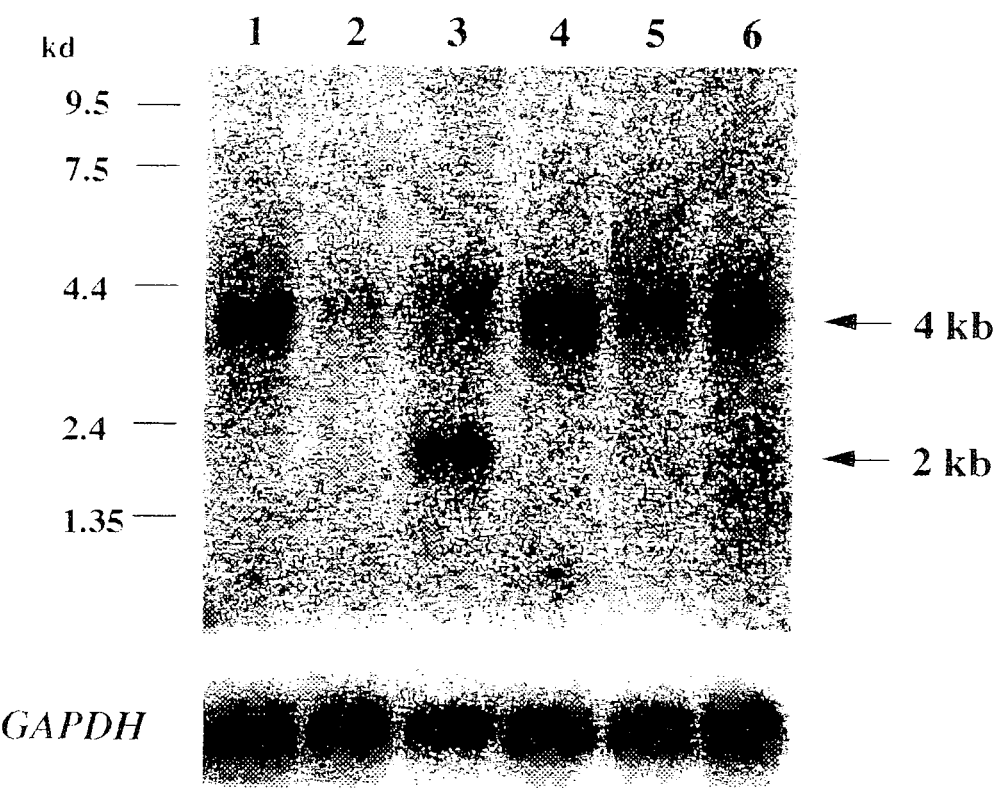

FIG. 4 shows the investigated results of down-regulated expression of the RecQ4 gene in cells from patients with Rothmund-Thomson syndrome. The transcripts of the RecQ4 gene from cells derived from patients with Rothmund-Thomson syndrome were compared with those from a healthy normal person. Poly(A)+ RNAs from skin fibroblast cells were prepared from patients with Rothmund-Thomson syndrome with mutations in the RecQ4 gene (II.3 and AG05013), from three other patients with Rothmund-Thomson syndrome (AG05139 and AG03587A from NIA, Aging Cell Repository; and TC4398 provided by Dr. R. Miller) who had no mutations in the RecQ4 gene, and from a healthy normal person. Northern blot analysis was performed on the RNAs prepared above using a probe prepared from the helicase domain of the RecQ4 gene. The mRNAs were also probed with GAPDH as an internal control. Each lane shows the corresponding results: lane 1, healthy normal person; lane 2, II.3; lane 3, AG05013; lane 4, AG05139; lane 5, AG03587; lane 6, TC4398.

Figure 5:
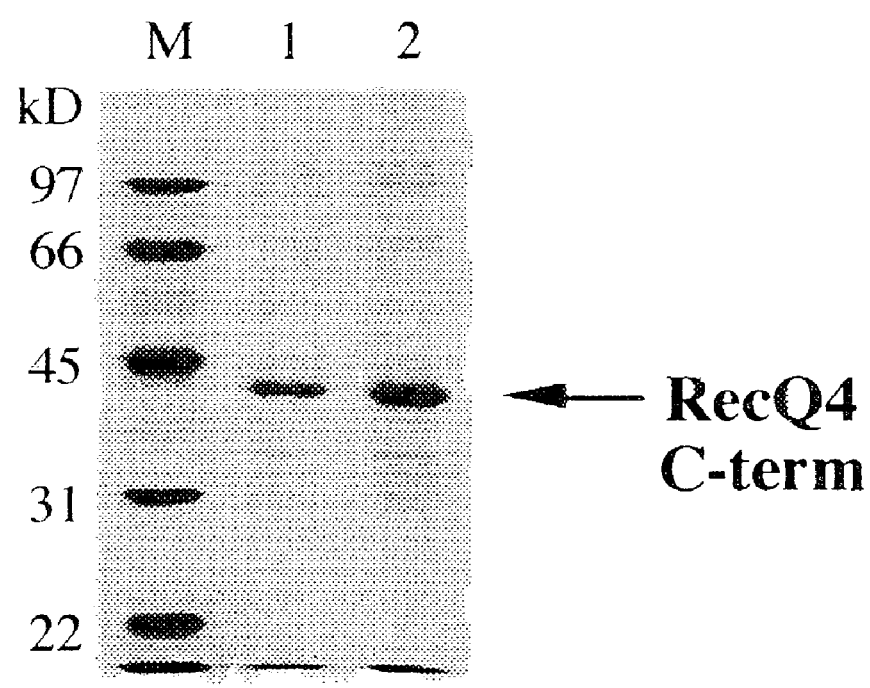

FIG. 5 shows a purified partial RecQ4 protein that was synthesized in *E. coli*. 302 amino acids from the C terminal region of RecQ4 were synthesized in *E. coli*. The purified and dialyzed protein was electrophoresed by SDS-PAGE and the gel was CBB-stained. The molecular weight was about 41 kD. Each lane shows the corresponding results: lane M, low molecular weight marker (1 µg); lane 1, purified protein (1 µl); lane 2, purified protein (2 µl).

Figure 6:
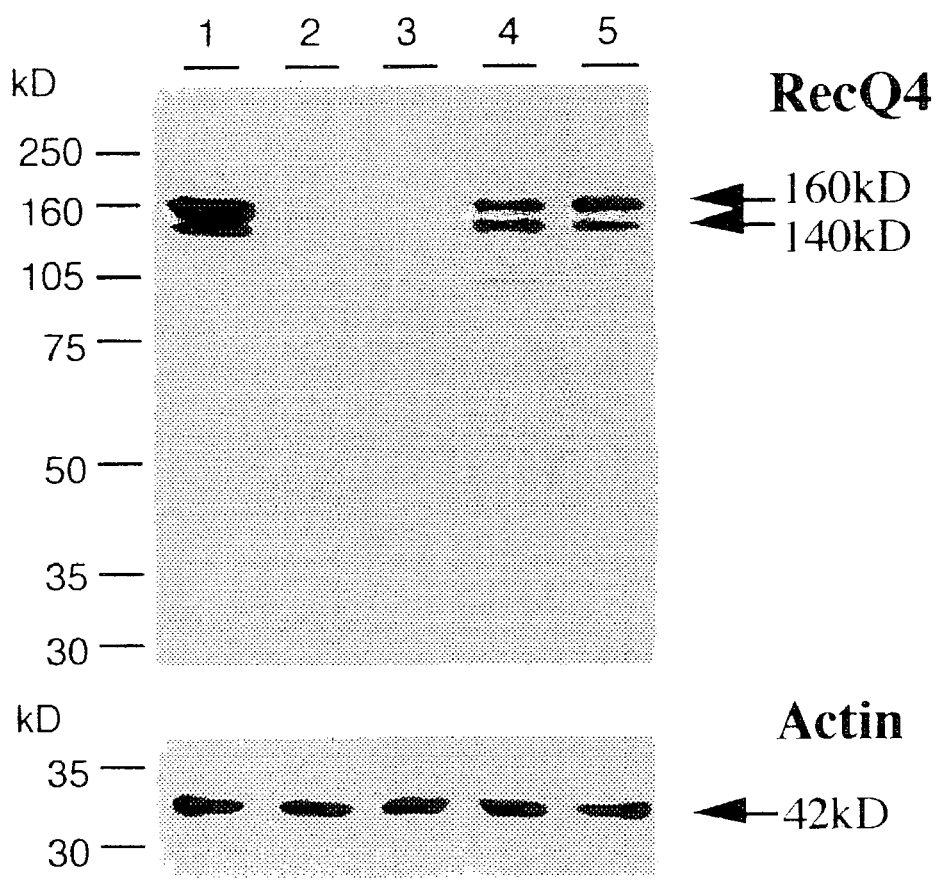

FIG. 6 shows the result of Western blot analysis using normal cells and cells from RTS patients. A 100-µg aliquot of each total cell extract was electrophoresed in a 7.5% polyacrylamide gel and subjected to Western blotting for RecQ4. A control experiment for total amount of protein was performed with 10-µg aliquots of the respective total cell extracts, which were analyzed by Western blotting for actin. Each lane shows the corresponding results: lane 1, WI38/SV40; lane 2, RTS-B (mut-1 and mut-2); lane 3, RTS-E (mut-3 and mut-4); lane 4, RTS-C (no mutation); lane 5, RTS-F (no mutation).

Figure 7:
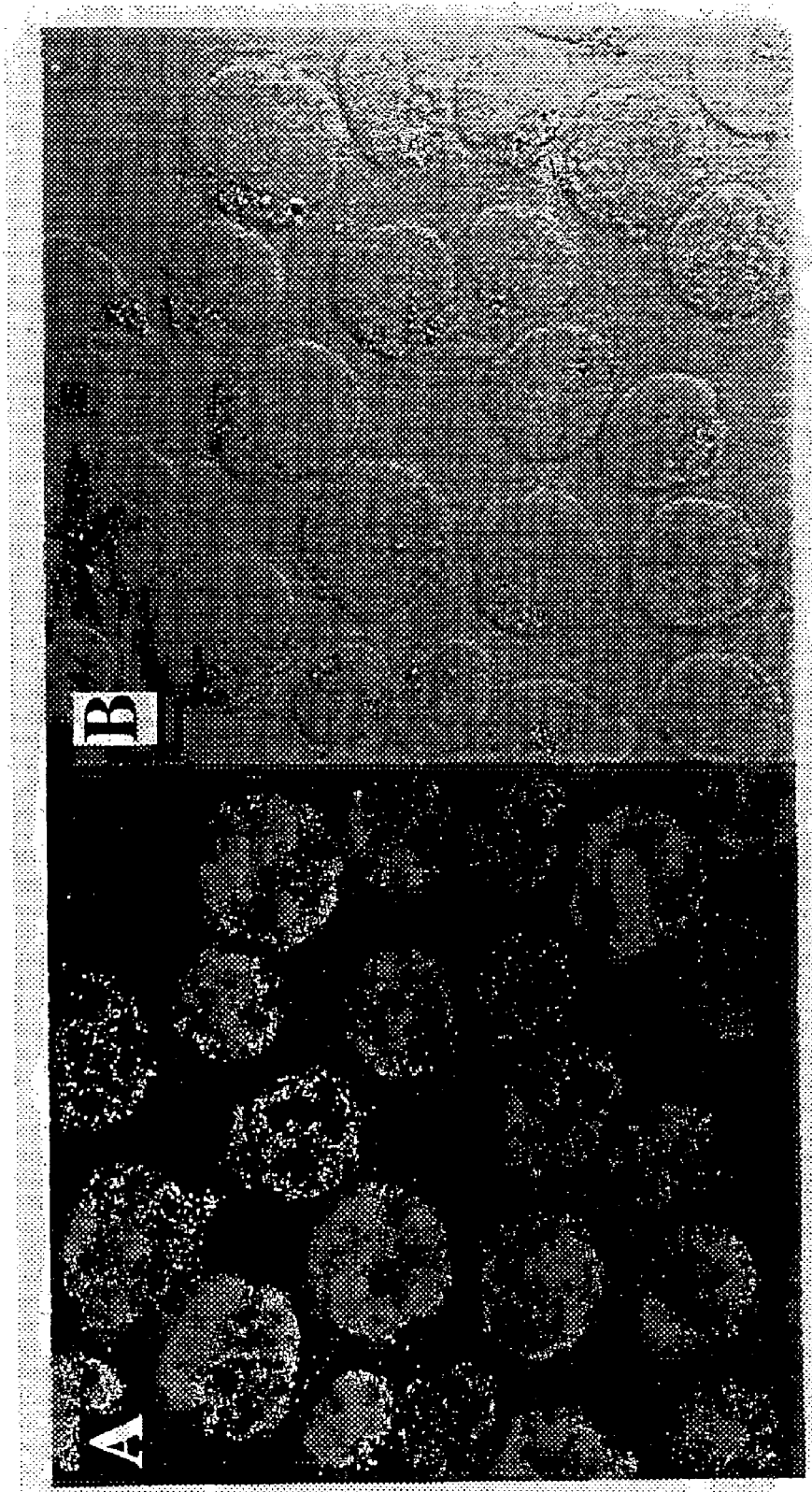

FIG. 7 shows an analysis for intracellular localization of RecQ4 by fluorescent antibody staining. K562 cells were attached onto a glass slide by using a Cytospin and immunostained with anti-RecQ4 antibody of 2 µg/ml (A). The morphology of cells can be recognized in (B), which was observed in the same visual field with transmitted light.

BEST MODE FOR CARRYING OUT THE INVENTION

The present invention is further illustrated in detail below with reference to the Examples, but is not to be construed as being limited thereto.

EXAMPLE 1

Genomic DNA Cloning of the RecQ4 Helicase Gene

The genomic DNA of the human RecQ4 helicase gene was obtained by screening a P1/PAC library. The P1/PAC library used was obtained from Genome Systems, and the preparation method is described in the Smoller et al. reference (Smoller, et al., Chromosoma, 1991, vol. 100, pp487–pp494). The screening was carried out by PCR using a sense primer, Q4P (5'-CGC TTC TGG AGA AAA TAC CTG CAC-3'/SEQ ID NO: 9), and an antisense primer, Q4Q (5'-TTG GAG CCT CCT CGT TCC CAC ACC-3'/SEQ ID NO: 10), corresponding to the base sequence segments in exon 21 of the RecQ4 gene. The screening was carried out in Genome Systems Co. The isolation and purification of DNA from P1 clone #13447 obtained in the screening was performed by the method as descried in the reference (Smoller, et al., Chromosoma, 1991, vol. 100, pp487–pp494). The genomic base sequence of the RecQ4 gene was determined by using the purified P1 DNA as the template. The determined base sequence of the genomic DNA encoding RecQ4 helicase (exon 1 to exon 21) is shown in SEQ ID NO: 2. The determination of the base sequence was performed by the PCR-based method described by Hattori et al. (Electrophoresis 13, pp560–565 (1992)). That is, the reaction was conducted by using a PRISM sequencing kit containing fluorescent dideoxy-terminator from Perkin-Elmer. Subsequently, the base sequence information was obtained in an automatic sequencer from Applied Biosystems (Model ABI 373), and then the data was analyzed by an attached Macintosh computer. RecQ4 gene-specific primers used for the base sequence determination are listed in Table 1.

TABLE 1

Q4 137S (5'-GTT TCC TGA ACG AGC AGT TCG ATC-3'/SEQ ID NO: 11)

Q4 714S (5'-GCT GCC TCC AGT TGC TTT TGC CTG-3'/SEQ ID NO: 12)

Q4 A2  (5'-TTG GTC GCA GCC CGA TTC AGA TGG-3'/SEQ ID NO: 13)

TABLE 1-continued

| | | |
|---|---|---|
| Q4 A3 | (5'-TGG CCC GTG GTA CGC TTC AGA GTG-3'/SEQ ID NO: 14) | |
| Q4 A5 | (5'-GAC GGC TGC GCG GGA GAT TCG CTG-3'/SEQ ID NO: 15) | |
| Q4 A9 | (5'-CTC AGC CCC TCC AGT CAA GCT AGG-3'/SEQ ID NO: 16) | |
| Q4 C5 | (5'-ACC AGT GCC TCA GGT GTC AGC-3'/SEQ ID NO: 17) | |
| Q4 C8 | (5'-GGA AAT GTG CTG GGA AAG GAG-3'/SEQ ID NO: 18) | |
| Q4 D5 | (5'-ACC AAG AGT CCA CTG CCT ACG-3'/SEQ ID NO: 19) | |
| Q4 D7 | (5'-GCT CCG TGG AGT TTG ACA TGG-3'/SEQ ID NO: 20) | |
| Q4 D9 | (5'-AGC GCA GCA CCA GGC TCA AGG-3'/SEQ ID NO: 21) | |
| Q4 D13 | (5'-GCA CTG CTT CCT GGG CCT CAC AGC-3'/SEQ ID NO: 22) | |
| Q4 E | (5'-GGG TAC AGC GAG CCT TCA TGC AGG-3'/SEQ ID NO: 23) | |
| Q4 E128 | (5'-CTC GAT TCC ATT ATC ATT TAC TGC-3'/SEQ ID NO: 24) | |
| Q4 F | (5'-CTG GGC AGG AGC GTG CAG TCA TGC-3'/SEQ ID NO: 25) | |
| Q4 G | (5'-AGG GGA GAG ACG ACC AAC GTG AGG-3'/SEQ ID NO: 26) | |
| Q4 H1 | (5'-TTA GGA TCC GGG GTG CTT GTG GAG TTC AGT G-3'/SEQ ID NO: 27) | |
| Q4 H2 | (5'-TTA GGA TCC CAG CTT ACC GTA CAG GCT TTG G-3'/SEQ ID NO: 28) | |
| Q4 K | (5'-TCC TGG CTG TGA AGA GGC TGG TAC-3'/SEQ ID NO: 29) | |
| Q4 L | (5'-ATC CCC CAA TGC AGT GCA GTC AGC-3'/SEQ ID NO: 30) | |
| Q4 U | (5'-AAT CTG GGA CCT CAC TGT GAC ATC-3'/SEQ ID NO: 31) | |
| Q4 Z | (5'-AGG GTG CCT TTC AGA TTG GCC TTG-3'/SEQ ID NO: 32) | |

The base sequence analysis revealed that the RecQ4 gene consists of 21 exons and 20 introns, and its full length is about 6.5 kb.

EXAMPLE 2

Cloning of the Promoter Region of the RecQ4 Helicase Gene

DNA from P1 clone #13447, containing the genomic DNA of the human RecQ4 helicase gene, was digested with restriction enzymes BamHI and BglII (TaKaRa Shuzo), and the plasmid vector pBluescriptII KS+ was digested with BamHI. The resulting digested DNAs were mixed with each other and then T4 DNA ligase (TaKaRa Shuzo) was added thereto for ligation reaction. E. coli competent cells, DH5α (Toyobo), were transformed with the reaction product and the resulting E. coli colonies were screened by PCR to determine whether or not the DNA from each colony contained a 5' upstream region of human genomic DNA of RecQ4. The screening for clones containing the 5' upstream region was carried out by using a sense primer, Q4 S (5'-TCA CAA CTT CTG ATC CCT GGT GAG-3'/SEQ ID NO: 5), and an antisense primer, Q4 R (5'-GAG GGT CTT CCT CAA CTG CTA CAG-3'/SEQ ID NO: 6), for amplifying a 247-bp segment of genomic DNA of RecQ4 sequence (residue 1399 to residue 1645). The bacteria were transferred from the colony into a PCR reaction solution using a toothpick. The following PCR experiment was conducted: denaturation at 95° C. for 5 minutes; 35 cycles of denaturation at 94° C. for 30 seconds, annealing at 55° C. for 30 seconds, and extension at 72° C. for 30 seconds; and final extension reaction at 72° C. for 5 minutes. After the reaction was completed, the PCR solution was analyzed by electrophoresis on a 2% agarose gel. The colony, in which a 247-bp band was detected, was judged to be positive. The bacteria derived from each of the resulting positive colonies were cultured in 3-ml LB medium. The alkali-SDS method was used to prepare plasmid DNA. Then the base sequence of the upstream region of the genomic DNA of RecQ4 was determined by using the plasmid DNA as a template and using the following primers: Q4 A14 (5'-CAA TGG GAG GCG TCA ACG TCA TCG-3'/SEQ ID NO: 7) and Q4 A15 (5'-GAG GCG AAA GAG CGG AGG GTC CAG-3'/SEQ ID NO: 8). The transcription initiation site of the RecQ4 gene was previously determined by cap-site PCR (Kitao, S. et al., Genomics, 1998, vol. 54, pp443–pp452; Japanese Patent Application No. Hei 9-200387). The cap-site PCR is a method for accurately determining the initial base in transcription. The transcription initiation site of the human WRN gene has also been determined by this method (Yamabe et al., Mol. Cell. Biol., 1998, vol. 18, pp6191–pp6200). The determined transcription initiation site corresponds to the first residue (residue 1) in the base sequence of genomic DNA of RecQ4 as well as in the base sequence of RecQ4 cDNA. The base sequence of upstream region of the RecQ4 gene was analyzed using the obtained genomic DNA. The analysis revealed a 5' upstream sequence of 679 bp (SEQ ID NO: 1) from the transcription initiation base.

EXAMPLE 3

Detection of Mutations in the RecQ4 Helicase Gene in Patients with Rothmund-Thomson Syndrome The inventors had previously cloned and analyzed two novel human helicase genes, RecQ4 and RecQ5, belonging to the RecQ helicase gene family (see Japanese Patent Application No. Hei 9-200387; Japanese Patent Application No. Hei 10-81492; and Kitao, S. et al., Genomics, 1998, vol. 54, pp443–pp452). Together, with these two novel genes, there are 5 members belonging to the human RecQ helicase gene family, including RecQ1 (M. Seki et al., Nucleic Acids Res. 22:4566 (1994); K. L. Puranam et al., J. Biol. Chem. 269:29838 (1994)), BLM (N. A. Ellis et al., Cell 83:655 (1995)), WRN(C.-E. Yu et al., Science 272:258 (1996)), RecQ4 and RecQ5.

Northern blot analysis for these five RecQ helicase genes revealed that, RecQ5, like RecQ1, was observed to be ubiquitously expressed through all the tissues and organs, while markedly high level expression was observed in the thymus and testis and high levels in the pancreas, small intestine and large intestine in a tissue-specific manner, like BLM and WRN for RecQ4. The fact that BLM and WRN are causative genes of Bloom syndrome and Werner syndrome, respectively, gave the thought that the RecQ4 gene was also involved in some diseases. The present inventors focused on Rothmund-Thomson syndrome, which exhibits similar symptoms to those of Bloom syndrome and Werner syndrome but for which the causative gene has not yet been identified. The inventors analyzed mutations in the RecQ4 gene using cells and DNA derived from two patients, (brothers) II.3 and II.6, who have previously been identified and reported as patients with Rothmund-Thomson syndrome by Lindor et al. (N. M. Lindor et al., Clin. Genet. 49:124 (1996)), cells and DNA from their parents and cells and DNA from patients with Rothmund-Thomson syndrome unrelated to the above-mentioned patients.

Specifically, full-length open reading frame of RecQ4 cDNA, as well as all exons of the RecQ4 gene, were first amplified by PCR from the two RTS patients, II.3 and II.6, and their parents reported by Lindor et al. to determine and compare the base sequences.

In order to amplify the full-length open reading frame of RecQ4 cDNA, total RNA was extracted from fibroblast cell lines derived from the two RTS patients by AGPC method (Chomczynski et al., Analytical Biochemistry, 1987, vol.162, pp.156–159), the mRNA was prepared from the total RNA by using Oligo(dT)30 cellulose beads, and subsequently, cDNA was synthesized through the reverse transcription (RT) reaction. PCR for amplifying the full-length open reading frame of RecQ4 cDNA was conducted as follows (Table 2):

TABLE 2

```
Composition of primary reaction
solution:
template DNA                              1 µl 20 µM each primer (A5/A7)           0.5 µl × 2

10 × buffer (Clontech)                  2.5 µl 2.5 mM dNTPs                              2 µl DMSO                                   1.25 µl
```

TABLE 2-continued

```
Klen Taq. polymerase (Clontech)         0.5 µl dH2O                                  16.75 µl (total volume 25 µl)

Composition of secondary reaction
solution:
template DNA                              1 µl 20 µM each primer (A6/A8)           0.5 µl × 2

10 × buffer (Clontech)                  2.5 µl 2.5 mM dNTPs                              2 µl DMSO                                   1.25 µl Klen Taq. polymerase (Clontech)         0.5 µl dH2O                                  16.75 µl (total volume 25 µl)

Reaction      1 × (94° C. 1 min)
condition:

5 × (94° C. 30 sec, 72° C. 4 min)

5 × (94° C. 30 sec, 72° C. 4 min)

25 × (94° C. 30 sec, 68° C. 4 min)

1 × (4° C. ∞)

Primer sequence
A5 5'-GAC GGC TGC GCG GGA GAT TCG CTG-3'/SEQ ID
No. 15

A6 5'-AGA TTC GCT GGA CGA TCG CAA GCG-3'/SEQ ID
No. 33

A7 5'-CAG GTT TTG CCC AGG TCC TCA GTC-3'/SEQ ID
No. 34

A5 5'-GTC ACT GGC CTA GCC TCT GAC AAC-3'/SEQ ID
No. 35
```

The resulting PCR product was excised from an agarose gel and purified. Then, the product was subcloned into a pCR2.1 vector (Invitrogen). The determination of the base sequence was performed by the PCR-based method described by Hattori et al. (Electrophoresis 13, pp560–565 (1992)). That is, the sequencing reaction was carried out using PRISM sequencing kit containing fluorescent dideoxy-terminator from Perkin-Elmer. Primers used for the determination of base sequence were as follows (Table 3):

TABLE 3

| | |
|---|---|
| Q4 A2 | (5'-TTG GTC GCA GCC CGA TTC AGA TGG-3'/SEQ ID NO: 13) |
| Q4 U | (5'-AAT CTG GGA CCT CAC TGT GAC ATC-3'/SEQ ID NO: 31) |
| Q4 T | (5'-TCA TCT AAG GCA TCC ACC CCA AAG-3'/SEQ ID NO: 36) |
| Q4 S | (5'-TCA CAA CTT CTG ATC CCT GGT GAG-3'/SEQ ID NO: 5) |
| Q4 A9 | (5'-CTC AGC CCC TCC AGT CAA GCT AGG-3'/SEQ ID NO: 16) |
| Q4 137S | (5'-GTT TCC TGA ACG AGC AGT TCG ATC-3/SEQ ID NO: 11) |
| Q4 F | (5'-CTG GGC AGG AGC GTG CAG TCA TGC-3'/SEQ ID NO: 25) |
| Q4 714S | (5'-GCT GCC TCC AGT TGC TTT TGC CTG-3'/SEQ ID NO: 12) |
| Q4 975S | (5'-GGA CAC AGA CCA GGC ACT GTT GAC-3'/SEQ ID NO: 38) |
| Q4 E | (5'-GGG TAC AGC GAG CCT TCA TGC AGG-3'/SEQ ID NO: 23) |
| Q4 K | (5'-TCC TGG CTG TGA AGA GGC TGG TAC-3'/SEQ ID NO: 29) |
| Q4 H2 | (5'-TTA GGA TCC CAG CTT ACC GTA CAG GCT TTG G-3'/SEQ ID NO: 28) |
| Q4 H1 | (5'-TTA GGA TCC GGG GTG CTT GTG GAG TTC AGT G-3'/SEQ ID NO: 27) |
| Q4 2314S | (5'-CAG GCC AGA CTC CAG GAT TGG GAG-3'/SEQ ID NO: 39) |

Subsequently, the base sequence information was obtained in an automatic sequencer from Applied Biosystems (Model ABI 373), and the data was analyzed by an attached Macintosh computer. The obtained base sequences of the full-length open reading frames from two RTS patients were compared with previously reported base sequence of RecQ4 cDNA (Japanese Patent Application No. Hei 9-200387) using base sequence editing software, DNA-SIS.

Subsequently, in order to amplify exons of the RecQ4 gene from genomic DNAs, cultured fibroblast cells, which were obtained from the two RTS patients, II.3 and II.6, and their parents, were washed with PBS, and then suspended in TNE buffer (50 mM Tris-HCl (pH 8.0), 100 mM NaCl, 1 mM EDTA). Then, an equal volume of TNE buffer, containing 2% SDS and 200 μg/ml Proteinase K, was added to each suspension and the resulting cell suspension was mixed by frequently turning it upside down at room temperature for 1 hour. The mixture was incubated at 42° C. overnight and then DNA was extracted from the mixture. The extracted DNA was treated 3 times with an equal volume of phenol to remove proteins. Subsequently, the sample was ethanol-precipitatedto give purified genomic DNA. By PCR usingeach genomic DNA as a template, the region containing exons 9, 10 and 11 of the RecQ4 gene was amplified using a sense primer, Q4 C8 (5'-GGA AAT GTG CTG GGA AAG GAG-3'/SEQ ID NO: 18), and an antisense primer, Q4 C5 (5'-ACC AGT GCC TCA GGT GTC AGC-3'/SEQ ID NO: 17); likewise, the region containing exons 13, 14 and 15 of the RecQ4 gene was amplified using a sense primer, Q4 E128 (5'-CTC GAT TCC ATT ATC ATT TAC TGC-3'/SEQ ID NO: 24), and an antisense primer, Q4 D1 (5'-CTC TTC ACA GCC AGG AAG TCC-3'/SEQ ID NO: 40). The following PCR reaction was conducted: denaturation at 95° C. for 5 minutes; 35 cycles of denaturation at 94° C. for 30 seconds, annealing at 60° C. for 30 seconds and extension at 72° C. for 60 seconds; and the final reaction at 72° C. for 5 minutes. The amplified DNA fragments were purified, and, using these DNAs as templates, the base sequence of the region containing exons 9, 10 and 11 in the RecQ4 gene was determined with Q4 C8 primer and the base sequence of the region containing exons 13, 14 and 15 in the RecQ4 gene was determined with Q4 D3 primer (5'-AGA GCT GGT GTC CCC GTG GAC-3'/SEQ ID NO: 41). The determination of base sequences was performed using a PCR-based method described by Hattori et al. (Electrophoresis 13, pp560–565 (1992)). That is, the sequencing reaction was conducted by using a PRISM sequencing kit containing fluorescent dideoxy-terminator from Perkin-Elmer. Subsequently, the base sequence information was obtained in an automatic sequencer from Applied Biosystems (Model ABI 373), and then the data was analyzed by an attached Macintosh computer. The obtained base sequences from patients and their parents were compared to each other by using the base sequence editing software, DNASIS.

Figure 1:
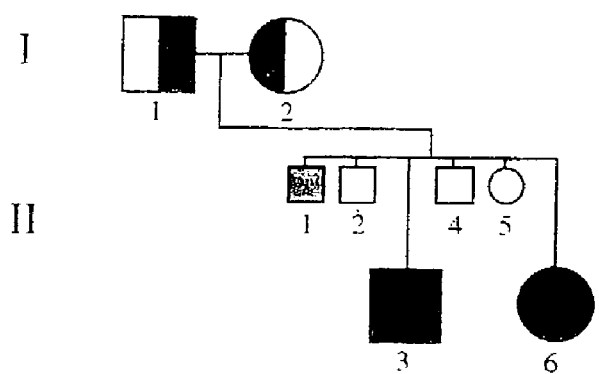
FIG. 1(a) shows a family tree of patients with Rothmund-Thomson syndrome and other members of the family. "I" represents parents; "1" indicates father and "2" indicates mother. Each of half-closed square and circle indicates a genetic carrier with a mutation in one allele of the RecQ4. "II" represents brothers or sisters (1–6) of the patients. Each of completely closed square (II.3, male) and circle (II.6, female) represents a patient with Rothmund-Thomson syndrome who has mutations in both alleles of the RecQ4 gene. II.2, II.4, and II.5 were not patients affected with Rothmund-Thomson syndrome and therefore no analysis was performed for them. The person II.1 indicated by the shaded symbol had been diagnosed as a patient with Rothmund- Thomson syndrome based on the clinical findings.
FIG. 1(b) shows the results of analysis for the mutation in the RecQ4 gene in the patients with Rothmund-Thomson syndrome and their parents. Lane I.1 represents the father; lane I.2, the mother; lane II.3, patient II.3; lane II.6, patient II.6. Based on the results, it has been revealed that the mother has a 7-base deletion (mut-1) in one allele of the gene inherited from her parent.
Figure 1:
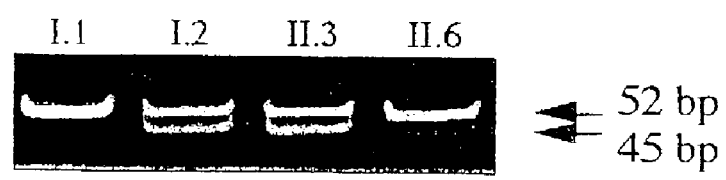
Figure 2:
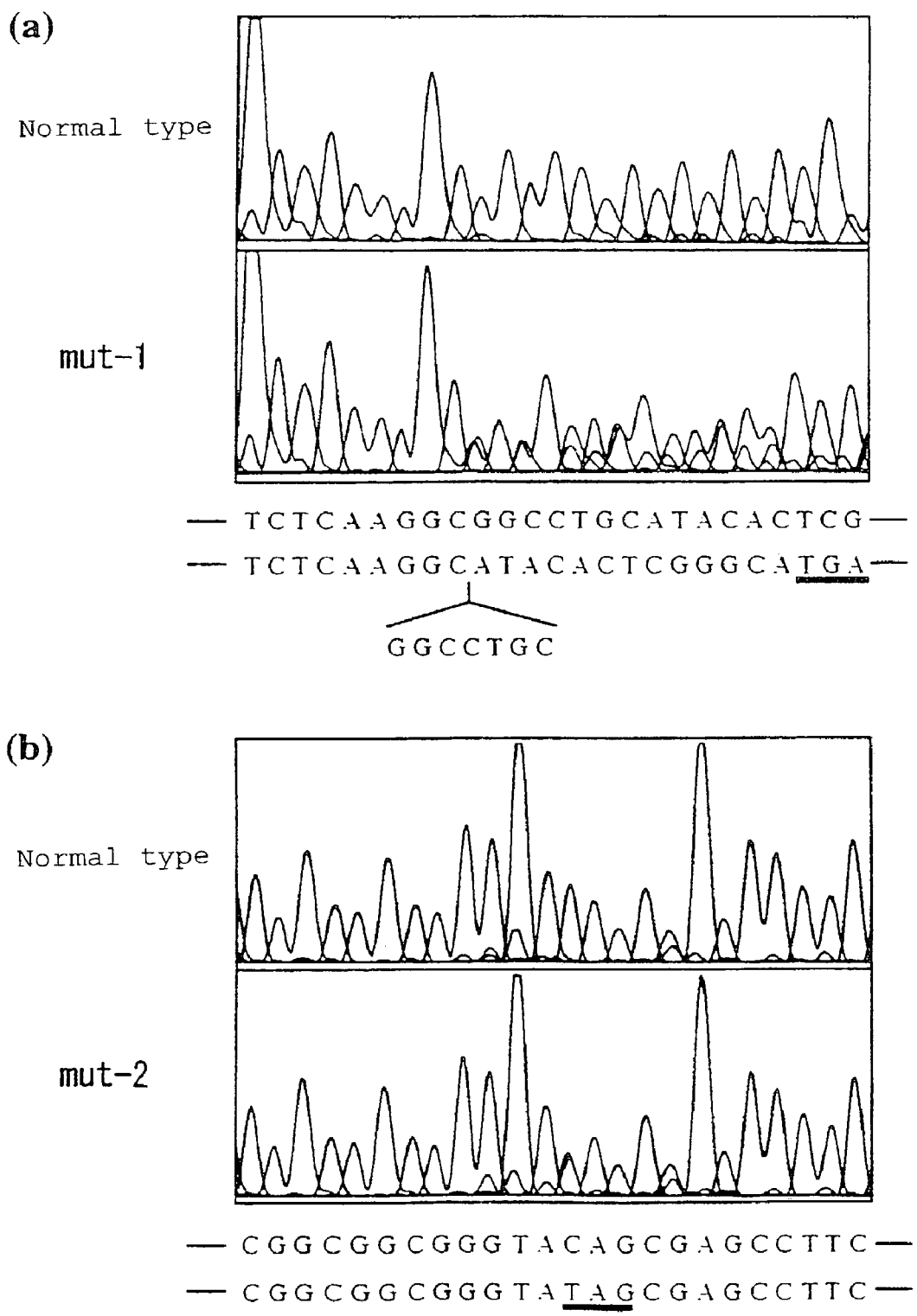
FIG. 2 shows the results of direct base sequencing analysis for the RecQ4 gene in its mutational region.

Based on the above-described base sequence analysis of the RecQ4 helicase gene, as described below, it has been clarified that both of the patients with Rothmund-Thomson syndrome in this family have heterozygous mutations. The family tree of the patients with Rothmund-Thomson syndrome is shown in FIG. 1(a), and the result of mutation analysis of in this family is shown in FIG. 1(b) and FIG. 2.

One mutation (referred to as mut-1) is present in exon 10, and it is a 7-base deletion (namely, GGCCTGC of position 1650–1656 in the base sequence of protein coding region (which corresponds to nucleotide 1734–1740 in SEQ ID NO: 3) (See FIG. 2(a)). This deletion causes frame shit, and as a result a termination codon TGA is generated 14-bases downstream of the deletion. Primers Q4 C1 (5'-TCT GGC CTG CCA CCG TGT CTC-3'/SEQ ID NO: 42) and Q4 C3 (5'-TGG TCA TGC CCG AGT GTA TGC-3'/SEQ ID NO: 43) were designed so that the mutation site of mut-1 was located between the two primers. The residue 1624–1675 in the protein coding region of the RecQ4 gene (position 1708–1759 in SEQ ID NO: 3) (52 bp) in each of DNAs from the parents (I.1 and I.2) and from the patients (II.3 and II.6) was amplified by PCR using these primers. The resulting DNA fragment was fractionated by electrophoretic separation in a 15% polyacrylamide gel to analyze the mutations. Thus, the presence of the mut-1 mutation was detected based on the difference in electrophoretic mobility (FIG. 1(b)). The analytical result showed that mut-1 was derived from the mother.

The other mutation (referred to as mut-2) is a point mutation from C to T at residue 2269 in the protein-coding region (position 2353 in SEQ ID NO: 3). The original codon CAG (Gln) has been converted to be a termination codon TAG (FIG. 2(b)). Both of mut-1 and mut-2 have mutations in the helicase domain of RecQ4 helicase, and it is presumed that the translation of transcripts for these defective genes is prematurely terminated, and these produce markedly smaller proteins (60 kDa and 82 kDa, respectively), as compared with the molecular weight of 133 kDa expected from the full length of the coding region for RecQ4 helicase. The results obtained by the mutation analysis are summarized in Table 4. The deduced truncated protein products are shown in FIG. 3. The same sequencing analysis was carried out by using DNAs prepared from other subjects belonging to this family. In this analysis, mut-1 was detected in patients II.3 and II.6 with Rothmund-Thomson syndrome as well as in I.2 cells derived from their mother; mut-2 was detected in patients II.3 and II.6 with Rothmund-Thomson syndrome as well as in I.1 cells derived from their father. That is, it was verified that mut-1 and mut-2 were derived from the mother and father, respectively, and the respective mutations had been inherited from the phenotypically healthy parents having single mutations.

In addition to these mutations specifically related to this family, another heterozygotic mutation has been found in the cell line derived from a patient with Rothmund-Thomson syndrome unrelated to the above-mentioned family. The cell line (No. AG05013) has been deposited in "Aging Cell Repository" of "National Institute of Aging (NIA)" in the USA. The mutation in the cell line were detected by amplifying the full-length open reading frame of RecQ4 cDNA and all exon regions of the RecQ4 gene by PCR, determining the base sequences thereof and comparing them with the normal sequence. Procedures for amplification of the full-length open reading frame of RecQ4 cDNA, subcloning and base sequence determination are as described above. In order to amplify exons of the RecQ4 gene from this patient, genomic DNA was prepared from fibroblast cells of the patient by the same method described above. By using the genomic DNA as a template, the region containing exons 14 and 15 of the RecQ4 gene was amplified by PCR using sense primer, Q4 D3 (5'-AGA GCT GGT GTC CCC GTG GAC-3'/SEQ ID NO: 41), and antisense primer, Q4 D2 (5'-TGG GAA CAC GCG CTG TAC CAG-3'/SEQ ID NO: 44). The region containing exons 12 and 13 of the RecQ4 gene was also amplified by PCR with sense primer, Q4 D11 (5'-GCC TCA CAC CAC TGC CGC CTC TGG-3'/SEQ ID NO: 45), and antisense primer, Q4 D12 (5'-GAC AGG CAG ATG GTC AGT GGG ATG-3'/SEQ ID NO: 46). The condition for PCR was as described above. The amplified DNA fragments were purified, and using the DNAs as templates, the base sequence of the region containing exons 14 and 15 in the RecQ4 gene was determined with Q4 D2 primer as well as the base sequence of the region containing exons 12 and 13 of the RecQ4 gene was determined with Q4 D1 primer. The results show that one of these mutations was a 2-base deletion (mut-3) and the other was a point mutation from G to T at the boundary between intron 12 and exon 13, which destroys the splicing donor consensus sequence (mut-4). It has been revealed that both mutations might cause frame shift for the translation downstream of the helicase domain, which respectively generate truncated protein products of 881 amino acids and 794 amino acids (Table 4 and FIG. 3).

TABLE 4

Rec Q4 gene mutations shown in RTS patients cell

| variant | mutation | exon | situation | deriviation |
|---|---|---|---|---|
| conjugated heterozygote | 1650 7 bases deletion (mut-1) | 10 | frameshift | Mexican-American |
| | C2269 (mut-2) | 14 | nonsense mutation | |
| conjugated heterozygote | 2492 2 bases deletion (mut-1) | 15 | frameshift | white |
| | C2269 (mut-2) | 13 | frameshift | |

In order to clarify whether or not the patients with Rothmund-Thomson syndrome carrying the mutations, mut-1 and mut-2, also have mutations in the WRN helicase gene or BLM helicase gene, poly(A)+RNAs from II.3 cells and AG05013 cells were reverse transcribed into cDNAs and base sequences were analyzed by amplifying the full-length open reading frames of the cDNAs by PCR, using the cDNAs as templates. The amplified region of WRN cDNA corresponded to the residues 188–4555 of GenBank accession No. L76937 and the region of BLM cDNA corresponded to the residues 57–4370 of GenBank accession No. U39817. However, no mutations were found in the WRN gene and BLM gene, which suggested that the WRN gene and BLM gene were not involved in Rothmund-Thomson syndrome. Based on the results described above, it can be concluded that mutations in the RecQ4 gene are associated with Rothmund-Thomson syndrome. Furthermore, the results suggest that neither normal WRN helicase nor normal BLM helicase can rescue the deficiency caused by the mutations in the RecQ4 gene in patients with Rothmund-Thomson syndrome.

As described above, the inventors performed mutational analysis for DNAs from 7 patients who had been clinically diagnosed as affected with Rothmund-Thomson syndrome, and found mutations in the RecQ4 gene in 3 patients including II.3 and II.6 belonging to the same family.

EXAMPLE 4

Northern Blot Analysis of the Cells From Patients with Rothmund-Thomson Syndrome To evaluate the relationship between mutations in the RecQ4 gene and pathogenesis of Rothmund-Thomson syndrome from a different viewpoint, RecQ4 mRNA from cells derived from 5 patients with Rothmund-Thomson syndrome were compared with that from a healthy normal person by Northern blot analysis (FIG. 4). Total RNA was first extracted from fibroblast cells from patients by AGPC method (Chomczynski et al., Analytical Biochemistry, 1987, vol. 162, pp156–pp159), and poly(A)+ RNA was purified from the resulting total RNA by using oligo(dT) latex beads. The poly(A)+ RNA (5 µg) was electrophoresed on a 1% agarose gel and then denatured with an alkaline solution. Then, the RNA was transferred onto a nylon filter. The 321-bp fragment consisting of residue 2013–2333 in the RecQ4 cDNA (GenBank accession No. AB006532) was amplified by PCR and then purified. The resulting fragment was radiolabeled with [$\alpha$-$^{32}$P] dCTP by using a Random Primer DNA Labeling Kit Ver.2 (TaKaRa Shuzo, code no. 6045) and used as a probe. The filter was incubated in a solution containing 5× SSPE buffer, 50% formamide, 2% sodium dodecyl sulfate (SDS), 10× Denhardt's solution, 100 µg/ml salmon sperm DNA, and 1×10$^7$ cpm/ml [$\alpha$-$^{32}$P]dCTP-labeled probe DNA at 42° C. overnight. Subsequently, the filter was washed 3 times with 2× SSC-0.1% SDS at room temperature and then washed with 0.2× SSC-0.1% SDS at 65° C. for 30 minutes. The radioactivity was detected by autography with a BAS1500 system (Fuji film).

The results show that the level of RecQ4 mRNA of about 4 kb was significantly reduced in fibroblast cells derived from II.3 (lane 2), as compared with that in fibroblast cells from healthy normal person (lane 1). Such specific reduction in the level of defective mRNA has also been observed in the expression of WRN gene in fibroblast cells derived from Werner patients and B lymphoblast-like cells transformed with Epstein-Barr virus (Y. Yamabe et al., Biochem. Biophys. Res. Commun. 236:151 (1997)). There are a number of reports indicating that nonsense codons influence RNA metabolism in vertebrate cells, that specific turnover of defective mRNA is stimulated and, as a result, similar downregulation of the expression can be found in other genetic diseases (L. E. Maquat, RNA 1:456 (1995); L. E. Maquat, Am. J. Hum. Genet. 59:279 (1996)). On the other hand, two types of mRNAs with normal and shorter sizes were detected in Northern blot analysis of mRNA prepared from the other patient (AG05013), carrying the heterozygotic mutations of the 2-base deletion and the point mutation at the 3'-splice site (FIG. 4, lane 3). The short mRNA is presumed to be the product of aberrant selective splicing, due to the mutation at the splice donor site, and is presumed to be the major molecular species for RecQ4 mRNA in this sample. On the other hand, transcripts of the RecQ4 gene, which were derived from three (lanes 4–6) of the remaining four patients with Rothmund-Thomson syndrome in whom no mutations had been found in the RecQ4 gene, were essentially the same as that from normal person (lane 1). These result, with respect to the transcript of the RecQ4 gene, is consistent with results obtained in the mutation analysis of DNA sequence. Thus, it was verified that mutations in the RecQ4 gene resulted in the disease in the patients with Rothmund-Thomson syndrome, II.3, II.6, and AG05013.

Diagnosis for Rothmund-Thomson syndrome on patients who are suspected to carry this disease have been previously based on relatively broad clinical findings and, thus, has been less accurate and less reliable. It is suggested that there may exist mutations in other genes (or other gene families) in the patients, in whom no mutations had been found in the RecQ4 gene, of the 7 patients with Rothmund-Thomson syndrome, or, alternatively, the diagnosis of Rothmund-Thomson syndrome may be wrong and in actuality the patient may be afflicted with another disease, one that exhibits similar clinical manifestations. In addition, there is a possibility that the clinical symptoms utilized as an index for the diagnosis of Rothmund-Thomson syndrome are too broad. The disease name "Rothmund-Thomson syndrome" is often used widely for patients exhibiting similar but ambiguous symptoms (E. M. Vennos et al., J. Am. Acad. Dermatol. 27:750 (1992); E. M. Vennos and W. D. James, Dermatol. Clinics. 13:143 (1995)). The diagnosis of Rothmund-Thomson syndrome can be made more accurately by utilizing gene diagnosis with the RecQ4 gene sequence.

EXAMPLE 5

Preparation of A-RecQ4 Helicase Monoclonal Antibody

A DNA fragment containing the nucleotides 2803 to 3711 of SEQ ID NO: 3, encoding the C terminal region of RecQ4, was inserted downstream to lac promoter/operator in an E. coli expression vector, pQE30 plasmid (QIAGEN). The plasmid DNA was transformed into an E. coli M15 strain containing a plasmid encoding lac repressor. The resulting transformant was cultured in LB medium (1% Bacto tryptone, 0.5% yeast extract, 0.5% NaCl, pH 7.0) containing 100 μg/ml ampicillin and 25 μg/ml kanamycin. Once the bacterial turbidity reached O.D.600=0.6–0.7, then 1 mM IPTG (isopropyl-β-D-thiogalactopyranoside) was added to the culture to induce expression.

The E. coli was harvested by centrifugation, and then lysed by sonication in Buffer A (50 mM Tris-HCl (pH 8.0), 2 mM EDTA, 0.1 mM DTT, 5 % glycerol, 1 mM PMSF) containing 2% NP-40. Then, centrifugal separation was repeated twice to obtain an insoluble precipitate. The resulting precipitated fraction was suspended in Buffer A, and mixed well with an equal volume of 1 M sucrose and 2 volumes of Percoll (SIGMA; colloidal PVP coated silica for cell separation). The mixture was treated by ultracentrifugation (Beckman ultracentrifuge L7-65, SW28 rotor, 20,000 rpm, 15° C., 30 min) to yield protein inclusion body in the lowest layer. The resulting sample was washed 4 times with 50 mM Tris-HCl (pH 8.0) and then dissolved in Buffer G (6 M guanidine-HCl , 0.1 M $NaH_2PO_4$, 0.01 M Tris, pH 8.0). The Buffer G was replaced with Buffer B (8 M-1 M urea, 0.1 M $NaH_2PO_4$, 0.01 M Tris, pH 8.0) by dialysis, and then further replaced with PBS. After the dialysis, the sample was concentrated by centrifugation in a conventional centrifuge concentrator/desalting device CENTRIPLUS 10 (Amicon). The above procedures provided a C terminal region (residue 2803–3711 in SEQ ID NO: 3; residue 907–1208 in SEQ ID NO: 4 (amino acid sequence)) recombinant protein of RecQ4 helicase (FIG. 5).

The purified recombinant protein (50 μg), mixed with Freund's complete adjuvant, was intraperitoneally given to BALB/c mice (7-week old, female) as primary immunization. 23 days after the primary immunization, the secondary immunization was carried out by intraperitoneal administration of the purified recombinant protein (50 μg) mixed with Freund's incomplete adjuvant. 30 days after the secondary immunization, the final immunization was performed by intravenous administration of the purified recombinant protein (25 μg). 3 days after, spleens was excised from the mice. The separated spleen cells and cells of NS-1 line were fused with each other in the presence of polyethylene glycol and suspended in HAT selection medium. 100-μl aliquots of the cell suspension were placed in wells of 96-well plates (560 wells in total) to cultivate the cells. In order to evaluate the antibody production in hybridomas, primary screening was performed by testing each culture supernatant in the 560 wells according to the antigen-solid-phase ELISA method using the purified recombinant RecQ4 helicase protein as the antigen. The result showed that 450 wells were positive. Among the wells, 55 wells that exhibited high values measured by ELISA were selected, and the corresponding cells were further cultured. The secondary screening was carried out in the same manner as in the primary screening according to the antigen-solid-phase ELISA method. All the 55 wells selected were evaluated as positive. The top fourteen wells in the measured values by ELISA were selected and the corresponding cells were treated by limiting dilution method to clone the hybridomas of interest. Hybridoma clones that were evaluated positive in ELISA were established as monoclonal antibody-producing clones. The established hybridomas were inoculated into BALB/c mice to prepare ascites, and purification of the antibody from the ascites was performed by the ammonium sulfate salting method. A clone K6314 was selected from the resulting 14 clones and the monoclonal antibody produced by this clone was further used as anti-RecQ4 helicase antibody in the experiments described below.

EXAMPLE 6

Western Blot Analysis of Cells From Patients with Rothmund-Thomson Syndrome

Western blot analysis for RecQ4 protein was carried out using human normal cells and cells from patients with Rothmund-Thomson syndrome. Primary cultured fibroblast cells, which had been isolated from a healthy normal person as well as from patients, were transformed with SV40 large T antigen to prepare strains of culture cells. These cultured cells were washed with PBS and then suspended in TNE (40 mM Tris-HCl (pH 7.5), 150 mM NaCl, 1 mM EDTA). The cells were harvested by centrifugation and then suspended in Lysis buffer (50 mM Tris-HCl (pH 8.0), 150 mM NaCl, 0.5% NP-40, 1 mM PMSF). The suspension was mixed by frequently turning it upside down at 4° C. for 30 minutes. After centrifugal separation, the resulting supernatant was obtained as the total cell extract. The concentration of protein was measured by using a Protein Assay DyeReagent Concentrate (BIO-RAD).

The prepared total cell extract was subjected to SDS-PAGE (SDS-polyacrylamide gel electrophoresis) according to the method of Laemmli (Laemmli (1970) Nature, vol. 227, p680–685)). Proteins were fractionated on a gel by electrophoresis and then were electrophoretically transferred from the gel onto a nitrocellulose filter (Imobilon transfer membrane; MILLIPORE) in a transfer buffer (20% methanol, 4.8 mM Tris, 3.9 mM glycine, 3.75% SDS) by using a TRANS-BLOT SD (BIO-RAD) at 20-V at room temperature for 1 hour. Blocking of this filter was carried out in PBS containing 5% skimmed milk. The filter was incubated with the primary antibody at room temperature for 2 hours and then washed with 0.05% Tween 20/PBS solution (PBS-T). Subsequently, the filter was incubated with the secondary antibody at room temperature for 1 hour and then washed with PBS-T. Then signal detection was carried out by using ECL Western blotting detection reagents (Amersham).

The primary antibodies used were 2 µg/ml anti-RecQ4 helicase mouse monoclonal antibody K6314 and 0.2 µg/ml anti-actin goat polyclonal antibody sc-1616 (Santa Cruz Biotechnology) in PBS solution; the secondary antibodies were Horseradish peroxidase-conjugated anti-mouse immunoglobulin rabbit polyclonal antibody (0.65 µg/ml; DAKO) and 0.25 µg/ml anti-goat immunoglobulin rabbit polyclonal antibody in 5% skimmed milk/PBS solution. Two bands, the molecular weight of which are about 160 kD and about 140 kD, were detected in Western blot analysis of total cell extract from normal cells (WI38/SV40) (FIG. 6, lane 1). The size, 160 kD, is larger than 133 kD predicted from the number of amino acids (1208 amino acids) encoded by the RecQ4 gene, suggesting the possibility that the helicase is modified, e.g. phosphorylation, at the protein level.

RecQ4 helicase protein was undetectable in RTS-B and E cells from the patients with the antibody against the C terminus, as expected from the result of mutation analysis (FIG. 6, lanes 2 and 3). Based on the above-described results, it was confirmed that the monoclonal antibody K6314 specifically recognizes the RecQ4 helicase protein. Further, in RTS-C and F, which are derived from patients with Rothmund-Thomson syndrome in whom no mutations were detected in the RecQ4 gene, RecQ4 helicase protein was detected as in normal cells (FIG. 6, lanes 4 and 5). These results indicate that Western blot analysis using anti-RecQ4 helicase monoclonal antibody K6314 can be utilized to immunologically diagnose the presence of mutations in the RecQ4 gene in patients who have been diagnosed as affected with Rothmund-Thomson syndrome.

EXAMPLE 7

Immunostaining of Cultured Cells by a Method Using Fluorescent Antibody

Intracellular localization of RecQ4 protein was analyzed by fluorescent antibody staining using the above-mentioned K6314 antibody. $0.5 \times 10^5$ cells (logarithmic growth phase) of cell line K562 derived from human chronic myelogenous leukemia were attached on a glass slide (MATSUNAMI GLASS; APS-Coated Micro Slide Glass) by using a Cytospin (TOMY SEIKO; centrifugal floating cell collector, MODEL SC-2). The cells were fixed in a solution of 3.7% formaldehyde/PBS at room temperature for 10 minutes, and then washed with PBS-T (0.05% Tween 20/PBS solution). The cell membrane permeability was enhanced in a solution of 0.1% Triton X-100/PBS at room temperature for 5 minutes. The glass slide was blocked in PBS containing 3% skimmed milk at room temperature for 1 hour and then incubation with the primary antibody was carried out in a solution containing 5 µg/ml anti-RecQ4 antibody K6314/PBS, 0.1% BSA and 0.05% $NaN_3$ at 4° C. overnight. The glass slide was washed with PBS-T, and then incubation with the secondary antibody was performed in a solution containing 7.5 µg/ml biotin-labeled anti-mouse immunoglobulin antibody (Chemicon) at room temperature for 1 hour. After washing with PBS-T, the glass slide was incubated in a solution of 5 µg/ml FITC-labeled streptavidin (Pharmingen) at room temperature for 1 hour and then washed with PBS-T. A solution of 2 µg/ml DAPI/50% glycerol was used to mount the sample and was counterstained for chromosomes by DAPI. Microscopic examination was carried out with an Olympas laser scanning biological microscope, FLUOVIEW system BX50.

In this observation, RecQ4 protein was detected as a very fine grain over the entire nucleoplasm (FIG. 7). This result suggests that the RecQ4 protein functions in the nucleus and also that the K6314 antibody is useful in the analysis of the functions of RecQ4 helicase.

INDUSTRIAL APPLICABILITY

The present invention reveals that Rothmund-Thomson syndrome is a genetic disease caused by mutations in the RecQ4 helicase gene. This finding makes it possible to conduct diagnostic tests for Rothmund-Thomson syndrome, including diagnose of a disease as Rothmund-Thomson syndrome and prenatal diagnosis for Rothmund-Thomson syndrome, and to perform treatments for Rothmund-Thomson syndrome, including gene therapy, by utilizing the RecQ4 helicase gene, primers or probes designed based on the sequence thereof, RecQ4 helicase, and antibodies thereto.

The invention claimed is:

1. A diagnostic agent for Rothmund-Thomson syndrome, wherein the agent comprises a monoclonal antibody which specifically binds to a RecQ4 helicase of SEQ ID No: 4, wherein said antibody binds to amino acids 907–1208 of SEQ ID No: 4.

* * * * *